US012591307B2

(12) United States Patent
Thielen et al.

(10) Patent No.: US 12,591,307 B2
(45) Date of Patent: Mar. 31, 2026

(54) APPARATUS AND METHOD FOR DETERMINING AN INTENT OF A USER

(71) Applicant: IDUN TECHNOLOGIES AG, Opfikon (CH)

(72) Inventors: Moritz Thielen, Stäfa (CH); Andrea Luca Fümm, Zürich (CH); Huy Cao Tri Do, Zürich (CH); Wadda Benjamin Du Toit, Zürich (CH); Séverine Gisin, Engelberg (CH)

(73) Assignee: IDUN TECHNOLOGIES AG, Opfikon (CH)

( * ) Notice: Subject to any disclaimer, the term of this patent is extended or adjusted under 35 U.S.C. 154(b) by 0 days.

(21) Appl. No.: 18/726,341

(22) PCT Filed: Jan. 5, 2023

(86) PCT No.: PCT/EP2023/050197
§ 371 (c)(1),
(2) Date: Jul. 2, 2024

(87) PCT Pub. No.: WO2023/131659
PCT Pub. Date: Jul. 13, 2023

(65) Prior Publication Data
US 2025/0068238 A1 Feb. 27, 2025

(30) Foreign Application Priority Data

Jan. 5, 2022 (EP) ..................................... 22150353

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/1114* (2013.01); *A61B 5/163* (2017.08); *A61B 5/165* (2013.01);
(Continued)

(58) Field of Classification Search
CPC .......... G06F 3/015; G06F 3/012; G06F 3/013; G06F 3/165; A61B 5/1114; A61B 5/163;
(Continued)

(56) References Cited

U.S. PATENT DOCUMENTS 9,167,356 B2 * 10/2015 Higgins ................. H04R 25/40
9,829,708 B1 * 11/2017 Asada ..................... G06F 3/012
(Continued)

FOREIGN PATENT DOCUMENTS

CN 112507799 A 3/2021
EP 3353630 A1 8/2018
(Continued)

OTHER PUBLICATIONS

International Search Report and Written Opinion for International Search Report for PCT/EP2023/050197, mailed Mar. 29, 2023, (15 pages).
(Continued)

*Primary Examiner* — William Lu
(74) *Attorney, Agent, or Firm* — Kagan Binder, PLLC

(57) ABSTRACT

The present invention relates to an apparatus (10) for determining at least one intent of at least one user. The apparatus (10) includes an eye movement sensing device (19) configured to sense at least one eye movement signal from the user, the eye movement signal being indicative of at least one eye movement of the user, and a head movement sensing device (24) configured to sense at least one head movement signal from the user, the head movement signal being indicative of at least one head movement of the user. The apparatus (10) is configured to determine at least one degree of correlation between the eye movement signal and the head movement signal and to determine at least one intent of the user based on the determined degree of correlation. The invention further relates to a corresponding method.

13 Claims, 5 Drawing Sheets

(51) Int. Cl.
  *A61B 5/11*          (2006.01)
  *A61B 5/16*          (2006.01)
  *A61B 5/398*         (2021.01)

(52) U.S. Cl.
  CPC ............ *A61B 5/398* (2021.01); *A61B 5/6817*
    (2013.01); *A61B 5/7246* (2013.01); *A61B 5/7264* (2013.01); *G06F 3/012* (2013.01); *G06F 3/013* (2013.01)

(58) Field of Classification Search
  CPC ....... A61B 5/165; A61B 5/398; A61B 5/6817; A61B 5/7246; A61B 5/7264; G06V 10/764; G06V 40/19; G06V 40/20; H04R 5/033; H04R 1/1016; H04R 1/1041; H04S 7/304
  See application file for complete search history.

(56)             References Cited

U.S. PATENT DOCUMENTS

| | | | | |
|---|---|---|---|---|
| 11,338,106 | B2 * | 5/2022 | Fabry | A61B 5/1114 |
| 12,204,687 | B2 * | 1/2025 | Beavers | G06F 3/013 |
| 2015/0331240 | A1 * | 11/2015 | Poulos | G02B 27/017 |
| | | | | 345/8 |
| 2016/0210407 | A1 * | 7/2016 | Hwang | G16B 50/30 |
| 2016/0378182 | A1 * | 12/2016 | Nguyen | G06F 3/013 |
| | | | | 345/156 |
| 2017/0365101 | A1 * | 12/2017 | Samec | G06T 19/006 |
| 2019/0142349 | A1 * | 5/2019 | Schorey | A61B 5/11 |
| | | | | 600/546 |
| 2019/0174237 | A1 * | 6/2019 | Lunner | H04R 1/1041 |
| 2019/0253812 | A1 * | 8/2019 | Gallégo | A61B 5/398 |
| 2019/0265802 | A1 * | 8/2019 | Parshionikar | G06F 3/012 |
| 2020/0138364 | A1 * | 5/2020 | Fabry | A61B 5/0024 |
| 2021/0103336 | A1 * | 4/2021 | Li | G06F 3/012 |
| 2022/0133212 | A1 * | 5/2022 | Krueger | A61B 3/0041 |
| | | | | 600/301 |
| 2022/0276723 | A1 * | 9/2022 | Sirois | H04R 1/1041 |
| 2024/0377430 | A1 * | 11/2024 | Casillas | G01C 19/56 |
| 2025/0036195 | A1 * | 1/2025 | Fanelli | G06F 3/04845 |

FOREIGN PATENT DOCUMENTS

| | | | |
|---|---|---|---|
| WO | 2017053971 | A1 | 3/2017 |
| WO | 2021237368 | A1 | 12/2021 |

OTHER PUBLICATIONS

Matthies, "InEar BioFeedController a headset for hands-free and eyes-free interaction with mobile devices", Human Factors in Computing Systems, pp. 1293-1298, DOI: 10.1145/2468356.2468587; ISBN: 978-1-4503-1899-0; Apr. 27, 2013, (6 pages).

* cited by examiner

10

26

19

Eye movement sensing device

Electronics unit

Head movement sensing device

24

10

12

16

20

19

18

14

24

22

28

26

30

| | 50 | 52 | 54 | 56 | 58 |
|---|---|---|---|---|---|
| Horizontal Eye Movement | left/right | left/right | left/right | none | none |
| Head Movement | matching | none | inverted | left/right | none |
| Movement Classification | natural | unnatural | unnatural | unnatural | none |
| Intent | auditory | control | control | - | - |

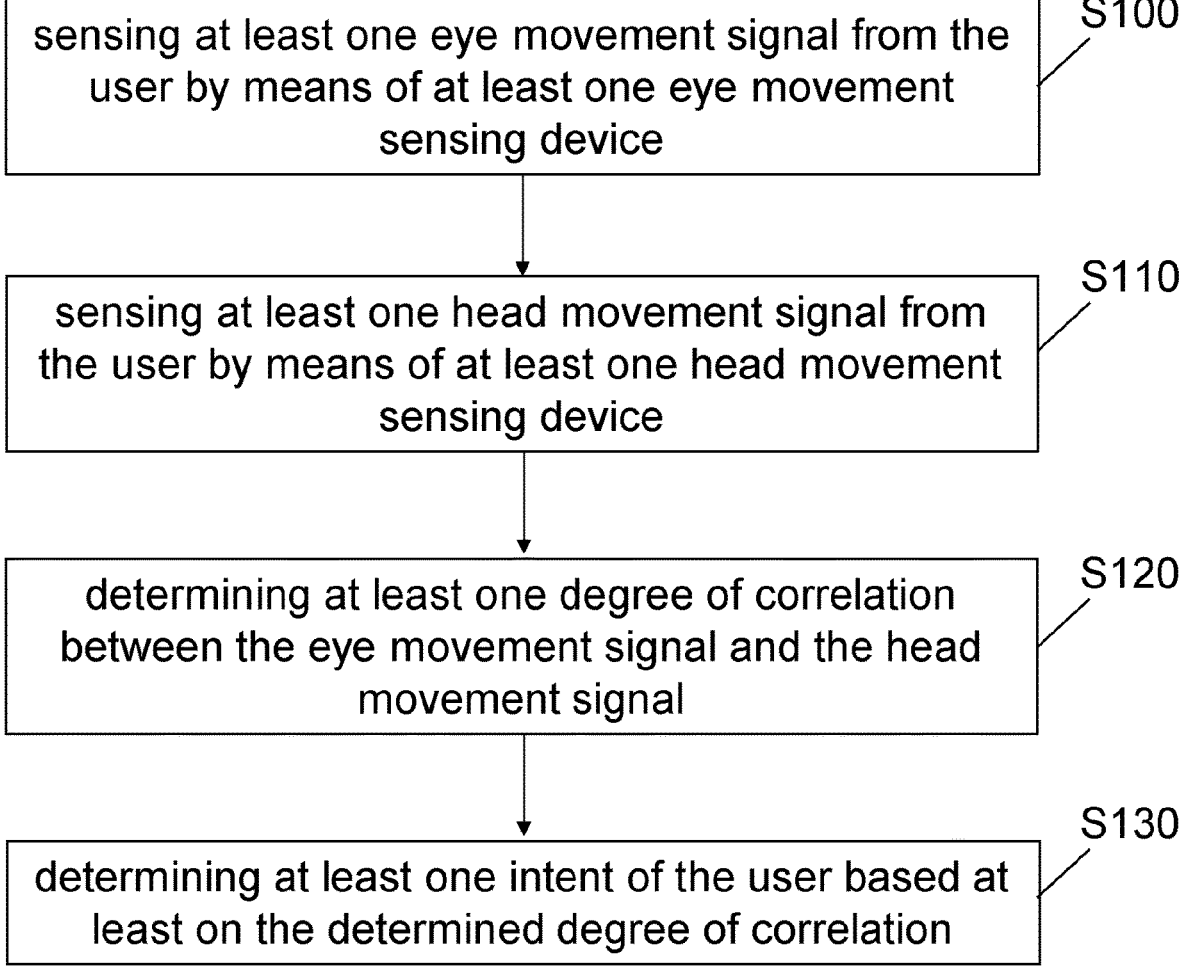

sensing at least one eye movement signal from the
user by means of at least one eye movement
sensing device

S100 sensing at least one head movement signal from
the user by means of at least one head movement
sensing device

S110 determining at least one degree of correlation
between the eye movement signal and the head
movement signal

S120 determining at least one intent of the user based at
least on the determined degree of correlation

APPARATUS AND METHOD FOR DETERMINING AN INTENT OF A USER

CROSS-REFERENCE TO RELATED APPLICATIONS

This application claims priority to International Application No. PCT/EP2023/050197, filed Jan. 5, 2023 and titled "APPARATUS AND METHOD FOR DETERMINING AN INTENT OF A USER," which in turn claims priority from a European Patent Application having Ser. No. 22150353.5, filed Jan. 5, 2022, both of which are incorporated herein by reference in their entireties.

Electronic devices, such as media devices, e.g., audio devices and/or visual devices, are employed in various fields for a variety of different uses and/or purposes. For instance, electronic devices may be useful for assisting humans in performing everyday tasks, such as by providing instructions and/or other information to the respective users of the electronic devices. Moreover, electronic devices are often used for leisure and/or entertainment purposes, e.g., to listen to audio content, such as music and/or podcasts, or to view visual content, such as pictures and/or virtual reality content and/or augmented reality content and/or films and/or other graphics, and/or to expand the space of actional inputs for human-machine-interaction.

For many years, electronic devices were conventionally configured to be controllable via one or more tangible control elements configured to be gripped and manually moved and/or actuated, e.g., by pushing, rotating or sliding said control elements, in order to control one or more functions of the electronic devices. Such tangible control elements may include buttons, sliders and/or knobs.

In order to improve user convenience and/or to reduce the obtrusiveness of such control elements, control functions have been electronically integrated into the respective electronic devices, in particular as virtual control elements, such as by implementing touch sensors, e.g., touch screens, into the electronic devices. However, such integrated virtual control elements still typically require haptic user input, e.g., by touching or at least moving a body part close to the touch sensor and/or touch screen.

As electronic devices have become more integrated into users' daily lives, e.g., as lifestyle devices and/or wearable devices, such as smart glasses and/or smartwatches, increased efforts have been made in recent years to provide the electronic devices with enhanced control technologies, e.g., to provide greater ergonomics and/or an enhanced user convenience and/or an enhanced user experience. For instance, manufacturers of visual devices and/or audio devices have developed various alternative ways of controlling various functions of the electronic devices, such as by detecting hand gestures or eye movement of the user.

However, the various control devices known from the prior art have one or more drawbacks. One disadvantage is that the control devices known from the prior art lack convenience for the user and/or are relatively complicated to operate which may lead to incorrect execution of the control procedure of the respective control device by the user. Moreover, the control devices known from the prior art are prone to being unreliable and/or inaccurate. For instance, the control devices known from the prior art may inaccurately and/or incorrectly detect the user's actual intent despite correction execution of the control procedure by the user, which may cause one or more functions of the electronic device to be unintentionally controlled and/or imprecisely controlled.

This may cause frustration and/or discontent of the user and/or may negatively influence the effects of the respective electronic device on the user, such as entertainment and/or relaxation, and/or at least reduce the positive effects of the respective electronic device on the user, e.g., productivity.

It is therefore an object of the present disclosure to provide an improved detection of a user intent.

This object is achieved by an apparatus defined by the features of claim 1. Preferred variations and further developments are defined by the features of the dependent claims.

The apparatus may be configured to determine at least one intent of at least one user. The apparatus may be configured to determine a plurality of intents of the user, simultaneously and/or sequentially. The apparatus may be configured to determine one or more intents of a plurality of users, simultaneously and/or sequentially. The intent of the user may be a target and/or a purpose of the user to achieve one or more specific effects, preferably physical effects, preferably in a virtual environment and/or a tangible environment of the user, such as in a visual and/or an audio environment and/or a lighting environment of the user. The intent of the user may be a level and/or a situation which the user desires and/or intends to achieve by actively and/or passively indicating the respective user intent, which is described in further detail below. The apparatus may be configured to detect, interpret and/or classify the intent of the user, and optionally further utilize and/or process and/or evaluate the user's intent.

The apparatus may include at least one eye movement sensing device configured to sense at least one eye movement signal from the user. The eye movement signal may be indicative of at least one eye movement of the user. The eye movement sensing device may be configured to perform eye tracking of one or both of the user's eyes, e.g., by detecting a gaze direction of the user. The eye movement sensing device may be any sensing device configured to detect the eye movement signal of the user from outside and/or inside the user's body in order to determine at least one eye movement of the user by means of the sensed eye movement signal. For this purpose of sensing the eye movement signal from the user, the eye movement sensing device may be configured to be attachable to the user's body, indirectly, e.g., via one or more attachment means and/or intermediate structures, and/or directly, e.g., without further attachment means and/or intermediate structures, such that the eye movement sensing device is positionable at least partially outside of the user's body and/or at least partially within the user's body.

An eye movement which may be sensed by the eye movement sensing device within the context of the present disclosure may refer to an active movement of the user's eye(s), i.e., that the eye movement of the user is sensed/detected by the eye movement sensing device as the user's eyes are moving. An eye movement which may be sensed by the eye movement sensing device within the context of the present disclosure may also refer to a position or orientation of the user's eye(s) relative to a neutral (centered) position of the user's eyes as the user's eyes are substantially still, i.e., not moving. Thus, an eye movement may be sensed by the eye movement sensing device after the user's eyes have moved, and are thus in a non-neutral position due to the eye movement, but are no longer actively moving.

Preferably, the eye movement sensing device includes at least one sensing region for sensing the eye movement signal from the user. The eye movement sensing device may be configured to sense and/or detect any movement of one eyeball or both eyeballs of the user, preferably a movement in which the eyeball(s) move(s) relative to the corresponding eye socket(s) of the user. The eye movement which can be sensed by the eye movement sensing device may be any type of rotational movement and/or translational movement of the user's eyeball(s), preferably including at least a horizontal eye movement of the user's eyeball(s). For the purpose of detecting a horizontal eye movement of the user's eyeball(s), the eye movement signal may include a horizontal electrooculographic (HEOG) signal. The eye movement, which can be sensed by the eye movement sensing device, may be in any one or more planes with respect to the user's body, preferably at least along a horizontal or transverse plane and/or a sagittal plane of the user's body. In most cases, humans generally move both eyeballs in unison. However, in some cases, both eyeballs may not be moved in unison. Instead, for instance, some humans can intentionally and/or unintentionally move their eyeballs at least partially independently from each other, e.g., in different directions, e.g., in a cross-eyed manner. The eye movement sensing device described herein may be configured to sense movement of both eyeballs of the user, even if the eyeballs are moved partially independently from each other.

The eye movement sensing device may be configured to contactlessly, e.g., optically, sense the eye movement signal from the user. Alternatively, or additionally, the eye movement sensing device may be configured to sense the eye movement signal from the user via contact to the user's body, e.g., via contact to the user's skin, e.g., within or near the user's ear(s).

The eye movement signal may be any signal which can be sensed from the user and which is indicative of at least one eye movement of the user. Preferably, the eye movement signal is a physiological signal, preferably a bioelectrical signal, preferably a biopotential signal, preferably an electroencephalographic (EEG) signal and/or an electrooculographic signal (EOG).

The apparatus may further include at least one head movement sensing device configured to sense at least one head movement signal from the user. The head movement signal may be indicative of at least one head movement of the user. The head movement sensing device may be any sensing device configured to detect the head movement signal from the user from outside and/or inside the user's body in order to detect or identify at least one head movement of the user by means of the head movement signal sensed by the head movement sensing device. The head movement sensing device may be configured to sense any head movement of the user, preferably a head movement which is relative to at least a portion of the user's upper body, e.g., the user's torso. The head movement sensing device may be configured to sense a head movement of the user which is substantially in unison with a movement of at least a portion of the user's upper body, e.g., the user's torso. The head movement sensing device may be configured to detect one or more absolute movements of the user's head, e.g., a turning movement, preferably a side to side turning movement, preferably about a longitudinal axis of the user, and/or a translational movement.

A head movement which may be sensed by the head movement sensing device within the context of the present disclosure may refer to an active movement of the user's head, i.e., that the head movement of the user is sensed/detected by the head movement sensing device as the user's head is moving. A head movement which may be sensed by the head movement sensing device within the context of the present disclosure may optionally also refer to a position or orientation of the user's head relative to a neutral (centered) position of the user's head as the user's head is substantially still, i.e., not moving. Thus, a head movement may be sensed by the head movement sensing device after the user's head has moved, and is thus in a non-neutral position due to the movement, but is no longer actively moving.

For the purpose of detecting or sensing the user's head movement, the head movement sensing device may be configured to be attached to at least a portion of the user's head such that the head movement sensing device is moved at least partially with the user's head. Alternatively, the head movement sensing device may be configured to be attached to at least a portion of the user's upper body such that the user's head is moved relatively to the head movement sensing device.

The head movement sensing device preferably includes at least one of the following devices configured to sense the user's head movement: at least one accelerometer, at last one gyroscope, at least one magnetometer, at least one angular rate sensor (ARS), at least one inertial measurement unit (IMU), at least one optical sensor, e.g., a camera, at least one infrared sensor, preferably a passive infrared sensor, and at least one microwave sensor.

The eye movement signal and/or the head movement signal may be processed in one or more processing steps, e.g., by means of one or more processing devices. The processing device may be any device capable of receiving and processing the eye movement signal and/or the head movement signal, e.g., to detect/determine an eye movement of the user from the eye movement signal and/or a head movement of the user from the head movement signal. The processing device may be configured to perform signal processing and/or signal interpretation, e.g., to the eye movement signal and/or the head movement signal, using heuristics and/or artificial intelligence, e.g., machine learning, deep learning and/or reinforcement learning.

The processing device may be a component of the apparatus described herein. Alternatively, or additionally, the processing device may be an external component, such as a personal device of the user, such as a wearable and/or mobile device of the user, such as a smartphone, a smartwatch, a pair of smart glasses, a tablet or other personal device of the user. The processing device may be communicatively couplable to the eye movement sensing device and/or the head movement sensing device, e.g., via a hard connection, e.g., via one or more wires, and/or via a wireless connection, e.g., via a Bluetooth connection.

The apparatus may be configured to determine at least one degree of correlation between the sensed head movement and the sensed eye movement of the user. Preferably, the apparatus is configured to determine a plurality of degrees of correlation between the sensed head movement and the sensed eye movement of the user. The apparatus is further configured to determine at least one intent of the user based at least on the determined degree of correlation. The correlation and/or the intent of the user may be determined by one or more processing devices, such as the processing device(s) described above. The processing device(s) may be integrated in an evaluating device which may be configured as an electronics unit. The apparatus, e.g., the electronics unit, may also include and/or may be connectable to a power source, such as one or more batteries, preferably rechargeable batteries, for providing power, preferably electrical power, to the apparatus, e.g., at least to the electronics unit.

The apparatus may be configured to determine and interpret an eye gesture and/or a head gesture as the intent of the user based on the determined correlation between the sensed eye movement signal and the sensed head movement signal.

By basing the determination of the user's intent on a correlation between the user's eye movement and the user's head movement, the use can intuitively, reliably and comfortably indicate the user's intent by actively and/or passively altering the correlation between the user's eye movement and the user's head movement, e.g., by intentionally altering the movement of the user's eye(s) relative to a head movement and/or vice versa. The apparatus may be configured to interpret different forms and/or degrees of alterations of movement of the user's eye(s) relative to a head movement and/or vice versa as one or more intents of the user, e.g., by using one or more algorithms and/or one or more lookup tables, e.g., by matching or classifying the determined correlation between the user's eye movement and the user's head movement with or into one or more, preferably predetermined, intents of the user. This may provide a more straightforward and/or convenient hands-free determination of user intent compared with the solutions known from the prior art.

Moreover, since the user can intentionally alter the correlation between the user's eye movement and the user's head movement according to an almost unlimited, or at least a relatively large, amount of possibilities, e.g., by altering the correlation between the user's eye movement and the user's head movement by various degrees and/or in various manners, e.g., in the direction and/or amount of movement of the user's eye(s) and the user's head, respectively, the user can express a plurality of different intents, e.g., to control and/or alter a plurality of different effects, preferably physical effects, preferably in a virtual environment and/or a tangible environment of the user, such as in a visual and/or an audio environment and/or a lighting environment of the user. This may increase the scope of use of the apparatus and may provide the user with an enhanced user experience, e.g., a greater control over an electronic media device by means of a plurality of identifiable intents of the user which can be used to control various functions of the respective electronic media device.

The apparatus may be configured to determine that the detected eye movement of the user matches and/or follows, i.e., naturally correlates with, the detected head movement, preferably within a certain, preferably predetermined tolerance range. The apparatus may be configured to classify such a determined natural correlation between the detected eye movement and the detected head movement of the user as being a natural movement of the user, e.g., with which the user does not intend to signal or indicate an intent. For the purpose of determining that the determined correlation between the detected eye movement and the detected head movement of the user is a natural correlation, the apparatus may have one or more references and/or criteria, which are preferably stored in the apparatus which the determined correlation must match, preferably within predetermined tolerances, and/or satisfy, respectfully. The one or more references or criteria may be stored in the apparatus, e.g., in a storage means of the apparatus, and/or may be stored externally, e.g., in an external storage, a server and/or a cloud.

The apparatus may be configured to determine that the detected eye movement of the user does not match, e.g., does not naturally correlate with, the detected head movement, i.e., that the detected eye movement and the detected head movement do not correspond to a natural head-eye movement, preferably outside of a certain, preferably a predetermined, tolerance range. The apparatus may be configured to classify such a determined unnatural correlation between the detected eye movement and the detected head movement of the user as being an unnatural movement of the user with which the user intends to signal or indicate an intent.

Alternatively, or additionally, the apparatus may be configured to classify/interpret a determined natural correlation between the detected eye movement and the detected head movement of the user as being a signal or indication of a user intent. Thus, a natural correlation and an unnatural correlation between the detected eye movement and the detected head movement of the user may each be classified/interpreted as being a signal or indication of a user intent, preferably as different user intents, e.g., to control and/or alter different effects, preferably physical effects, preferably in a virtual environment and/or a tangible environment of the user, such as in a visual and/or an audio environment of the user. For instance, natural and unnatural correlations between the detected eye movement and the detected head movement of the user may each be identified/interpreted as different intents of the user for controlling different functions of an electronic device, such as a media device and/or a smart device and/or an Internet of Things (IoT) device and/or a device which provides at least one stimulus to at least one of the user's senses, e.g., an audio, visual and/or haptic stimulus, or the same function in a different manner, e.g., changing the tracks being played by an audio device by skipping 1 or 2 tracks at a time according to the respective intent of the user determined by the apparatus described herein, respectively.

The apparatus may be configured to determine one or more confidence values, preferably to indicate the reliability of the determined user intent and/or confirm that a determined correlation between the sensed eye movement signal and the sensed head movement signal is to be interpreted as an expression of an intent of the user. For instance, the apparatus may be configured to determine that, if the determined correlation is within or outside a certain range, preferably a predetermined range, the user's eye movement and/or head movement are not intended to be an expression of an intent of the user. In this case, the apparatus may be configured to disregard the determined user intent. For instance, the apparatus may be configured to compare at least one amplitude of the eye movement signal with at least one predetermined amplitude value and/or at least one amplitude of the head movement signal with at least one predetermined amplitude value and determine, if the sensed eye movement and/or head movement, respectively, is intentional or unintentional. For instance, the eye movement signal and/or the head movement signal may be a current signal or a voltage signal and the amplitude may be an amplitude of the current signal and/or the voltage signal, respectively.

For the purpose of determining the correlation, the apparatus may be configured to compare the sensed eye movement signal and the sensed head movement signal within a certain time frame, preferably predetermined time frame, and/or within a certain epoch, preferably a predetermined epoch. Preferably, the correlation between the eye movement signal and the head movement signal must satisfy one or more criteria within said time frame for determining, and optionally classifying, the intent of the user.

The apparatus may be configured to determine the correlation between the sensed eye movement signal and the sensed head movement signal based on a time correlation between the sensed eye movement signal and the sensed head movement. For instance, a determined time shift between the eye movement signal and the head movement signal which exceeds a certain time shift threshold, preferably a predetermined time shift threshold, may indicate an unnatural correlation between the eye movement and the head movement of the user.

Alternatively, or additionally, the apparatus may be configured to determine the correlation between the sensed eye movement signal and the sensed head movement signal by classifying the correlation between the sensed eye movement signal and the sensed head movement into one or more events. Preferably, the one or more events include one or more of the following: a detected head movement of the user and a detected non-movement of the user's eye(s), a detected eye movement of the user and a detected non-movement of the user's head, a detected head movement of the user in a first direction and a detected eye movement of the user in a second direction, the first direction being substantially opposite, or at least substantially different, from the second direction. Each of the above-identified events may be interpreted as being a distinct intent of the user.

In order to determine an absolute direction in which the user's eye(s) and/or head is/are moved, the apparatus may include a reference. Providing such a reference may be based on the design of the apparatus itself. For instance, the apparatus may be configured such that the apparatus must or should be worn in a certain manner, e.g., a certain predetermined orientation, e.g., by informing the user via one or more labels on the apparatus. Alternatively, or additionally, the apparatus may be configured to perform a calibration prior to use, e.g., by instructing the user to turn the user's eye(s) and/or head in a certain direction. The apparatus may then determine and/or store the eye movement signal and/or the head movement signal which was sensed during the calibration as a reference for determining an absolute direction in which the user's eye(s) and/or head is/are moved and/or an absolute and/or relative degree by which the user's eye(s) and/or head is/are moved.

The apparatus may include at least one electronic module which may include one or more processing devices, such as the processing device described above, one or more amplifiers configured to amplify the eye movement signal, and/or at least one energy source, preferably at least one energy storage, preferably one or more batteries, preferably rechargeable batteries. Alternatively, or additionally, the electronic module and/or the head movement sensing device and/or the eye movement sensing device may be connectable to an external power source, such as a household power outlet. The electronic module may further include a transmitting device configured to transmit data, such as data related to the eye movement signal and/or the head movement signal, to an external device, such a personal device of the user, e.g., a smartwatch and/or a smartphone. For this purpose, the transmitting device may be configured to provide a connection, preferably a wireless connection, e.g., a Bluetooth connection, to the external device. The external device may be configured to evaluate and/or process the received data.

The apparatus may be configured to generate one or more control inputs, preferably control signals, based at least on the determined intent of the user, configured to control at least one electronic device, such as a control device and/or a device which provides at least one stimulus to at least one of the user's senses, such as a media device, e.g., an audio device, a visual device and/or a lighting device, to control one or more functions of an electronic device. The one or more control inputs may be configured to control one or more functions of the electronic device, such as one or more properties of at least one stimulus, e.g., an audio stimulus and/or a visual stimulus and/or a haptic stimulus, provided by the electronic device to the user, such as audio content, e.g., a particular genre of music or one or more particular songs, visual content, such as one or more visual effects, and/or a general like or dislike of the content of the electronic device. Preferably, the one or more control inputs may be configured to control one or more audio effects of an audio device, such as by altering a spatial distribution and/or a spatial variance of one or more properties of the audio provided by the audio device, e.g., a volume or sound intensity of the audio provided by the audio device to the user. For instance, the apparatus may be configured to generate one or more control inputs for controlling and/or altering a 3D or 2D soundscape based on the determined user intent. The user can thus comfortably and conveniently provide control commands via an expression of user intent according to the concepts described herein. The electronic device may be included by the apparatus described herein, i.e., as a component thereof. Additionally, or alternatively, the electronic device may be an external device.

Although the correlation described herein is based on a correlation between eye movement and head movement of the user, any correlation between two individually moveable body parts, such as generally between two different parts of the user's face, e.g., the user's eyeball and eyelid or the user's jaw and lip(s) or at least one limb and at least one digit, e.g., at least one finger, of the user, may be used to base the determination of intent of the user on.

Preferably, the apparatus is configured to be wearable on at least a portion of the user's body, preferably at least partially on the user's head and/or neck. This may enhance the user-friendliness and/or the comfort of the apparatus. For instance, by enabling the apparatus to be worn on at least a portion of the user's body, preferably at least partially on the user's head and/or neck, the apparatus may be carried on the user's body in a hands-free manner. In particular, configuring the apparatus to be worn at least partially on the user's head and/or neck may further enhance the wearability and/or comfort of the apparatus by allowing the torso and/or legs of the user, in particular the movement thereof, to be substantially unrestricted by the apparatus.

Preferably, the eye movement sensing device is configured to sense at least one bioelectrical signal, preferably a biopotential signal, preferably an electrooculographic (EOG) signal, from the user. The bioelectrical signal is preferably indicative of the at least one eye movement of the user. Bioelectrical signals are relatively dynamic and change relatively quickly upon changes in the physiology of the user, e.g., upon movements of the user's eyes. Thus, sensing bioelectrical signals to identify at least one eye movement of the user may provide signals which are relatively reliable and provide a relatively high responsiveness to eye movement(s) of the user. This may allow the intent of the user to be determined more quickly and/or more reliably.

Preferably, the eye movement sensing device includes at least one sensor region, preferably including at least two electrodes, made at least partially of an electrically conductive material. Alternatively, the eye movement sensing device includes at least two sensor regions, each preferably including at least one electrode, made at least partially of an electrically conductive material. The sensor region may be configured to sense the eye movement signal.

Preferably, at least a portion of the eye movement sensing device is configured to be inserted at least partially into a cavity of the user's ear such that the sensor region contacts at least a portion of the user's ear anatomy within the cavity. This may enable the eye movement signal to be sensed at least partially in and/or near the user's ear and may enable the eye movement sensing device to be attached to and/or in the user's ear, which may further increase the wearability and/or wearing comfort of the apparatus.

Preferably, the eye movement sensing device includes at least two eye movement sensing components each having at least one sensor region, preferably including at least two electrodes, made at least partially of an electrically conductive material. Alternatively, the eye movement sensing device includes at least two eye movement sensing components each having at least two sensor regions, each preferably including at least one electrode, made at least partially of an electrically conductive material. Preferably, the eye movement sensing components may be manoeuvrable relative to each other. Thus, each eye movement sensing component may be positioned separately on the user's body, for instance, by positioning one eye movement sensing component on or at least partially in a user's first ear and positioning another eye movement sensing component on or at least partially in a user's second ear.

Preferably, at least a portion of each eye movement sensing component is configured to be inserted at least partially into a cavity of one of the user's ears, respectively, such that the respective sensor region contacts at least a portion of the user's ear anatomy within the respective cavity. The cavity may be an ear canal and/or a concha of the user's ear(s).

The sensor regions of the eye movement sensing components may be configured as one or more channels for providing data to the apparatus. For instance, the sensor region(s) of a first eye movement sensing component may be configured as sensing channel(s), e.g., sensing channels 1 and 2 for sensing the eye movement signal, and the sensor region(s) of a second eye movement sensing component may be configured as a ground and/or a reference. However, other distributions of channels are also possible. The apparatus may have any number of sensor regions.

Preferably, the eye movement sensing components are communicatively interconnected. For instance, the eye movement sensing components may be communicatively interconnected via one or more wires and/or via a wireless connection, e.g., via a Wifi network and/or a Bluetooth connection and/or a cloud and/or a server, etc. Preferably, the eye movement sensing components are communicatively connected to an evaluating device. Preferably, the evaluating device has at least one processing device configured to process the eye movement signal and/or the head movement signal.

Preferably, the apparatus includes at least one earpiece configured to be worn on the user's ear(s) and/or over the user's ear(s) and/or at least partially within a cavity of the user's ear(s). Preferably, the earpiece includes at least the eye movement sensing device and/or the head movement sensing device. The earpiece may enable a least a portion of the apparatus, preferably the eye movement sensing device and/or the head movement sensing device, to be mounted to the user's ear(s). This may further enhance the wearability and/or user convenience of the apparatus described herein. Preferably, the earpiece includes at least one audio driver and/or audio speaker for generating one or more sounds, preferably music and/or speech.

Preferably, the earpiece includes at least one eartip configured to be inserted at least partially into a cavity of the user's ear. The eartip may include at least the eye movement sensing device. Preferably, the eartip is configured such that the eye movement sensing device is at least partially inserted into the cavity of the user's ear, when the eartip is inserted at least partially into the cavity of the user's ear. Preferably, the eartip includes at least one sensor region configured to sense the eye movement signal from the user. Preferably, the sensor region is configured to be positioned at least partially within the ear canal and/or within the concha of the user's ear, when the apparatus is in a normal wearing state. Preferably, the eartip is configured to be connectable, preferably releasably connectable, to an earbud.

Preferably, the apparatus includes at least one earbud configured to be inserted at least partially into a cavity of the user's ear. Preferably, the earbud includes at least the eye movement sensing device and/or the head movement sensing device. Preferably, the eartip includes at least one sensor region configured to sense the eye movement signal from the user. Preferably, the sensor region is configured to be positioned at least partially within the ear canal and/or within the concha of the user's ear, when the apparatus is in a normal wearing state.

Preferably, the apparatus is configured to classify the intent of the user by determining whether the determined degree of correlation satisfies at least one criterion. For the purpose of classifying the intent of the user, the apparatus may include a classifying device or classifying module configured to classify the intent of the user by determining whether the determined degree of correlation satisfies one or more criteria. The classifying device may include and/or may be integrated in a processing device, such as the processing device described above, configured to process the eye movement signal and/or the head movement signal to determine the degree of correlation between the eye movement signal and the head movement signal. The classifying device may be configured to determine if the degree of correlation satisfies at least one criterion. If the classifying device determines that the degree of correlation satisfies the criterion, the classifying device may classify the intent of the user, e.g., as an intent of the user to control one or more functions of an electronic device, e.g., to control an audio content and/or a visual content of the electronic device. The apparatus may be configured to classify the intent of the user into a plurality of different classes or events based on a plurality of criteria which the determined degree of correlation must satisfy in order to be classified into the respective class.

Preferably, the apparatus is configured to determine whether the determined correlation is a natural correlation between the sensed eye movement and the sensed head movement of the user or an unnatural correlation between the sensed eye movement and the sensed head movement of the user according to at least one criterion to classify the intent of the user based thereon. For instance, if the apparatus detects, by means of the eye movement sensing device, that eye movement is performed by the user, and the apparatus detects no, or only minimal, head movement, then the apparatus may be configured to determine that the correlation between the sensed eye movement and the sensed head movement of the user is an unnatural correlation.

Preferably, the apparatus is configured to determine a natural correlation between the sensed eye movement and the sensed head movement of the user by determining a threshold for a minimum degree of head movement of the user based on the sensed eye movement of the user and determining if the threshold is reached and/or surpassed by the sensed head movement. The threshold may provide a minimum level of positive correlation between movement of the user's head and movement of the eye(s), i.e., the user's eyes follow the user's head to at least a minimum degree, to determine if the user's head-eye is natural, i.e., when the user does not intentionally deviate from a natural head-eye movement to indicate an intent. Thus, for instance, if the user's eye(s) are moved by a certain degree, which may be sensed by the eye movement sensing device by sensing the eye movement signal, then the apparatus may be configured to determine a threshold for a minimum degree of head movement of the user based on the sensed eye movement of the user to classify the correlation as a natural correlation. If the threshold is reached and/or surpassed by the sensed head movement, the degree of correlation may be determined by the apparatus as being natural. If the threshold is not reached by the sensed head movement, the degree of correlation may be determined by the apparatus as being unnatural, since the sensed head movement does not follow the sensed eye movement in a natural manner. The apparatus may be configured to determine that the user intentionally deviates from a natural head-eye movement to indicate an intent, e.g., to control one or more functions of an electronic device.

Preferably, the apparatus is configured to determine a natural correlation between the sensed eye movement and the sensed head movement of the user by determining a direction of the sensed head movement of the user and a target direction of head movement of the user based on the sensed eye movement of the user and determining if the determined direction of the sensed head movement of the user and the target direction of head movement of the user substantially match and/or are within a target range. Thus, for instance, if the user's eye(s) are moved in a certain direction, which may be sensed by the eye movement sensing device by sensing the eye movement signal, then the apparatus may be configured to determine if the direction of head movement of the user, which may be sensed by the head movement sensing device, substantially follows the direction of the user's eye movement. In case the apparatus determines that the direction of head movement of the user does not substantially follow the direction of the user's eye movement, then the apparatus may determine that the user is intentionally deviating from a natural head-eye movement to indicate an intent, e.g., to control one or more functions of an electronic device.

Preferably, the apparatus is configured to determine a first intent, when the determined correlation satisfies at least one first criterion, and a second intent, when the determined correlation satisfies at least one second criterion. Preferably, the first criterion differs from the second criterion and/or the first intent differs from the second intent. The first intent may be an auditory intent, e.g., what the user wants to hear and/or see from an electronic device, and the second intent may be an active control content, e.g., the user wants to change a scene and/or track or adjust a volume. This may enable the apparatus to determine and distinguish between a plurality of intents of the user which may enable the user to indicate a plurality of intents, e.g., to control a plurality of different functions of an electronic device, e.g., by interpreting an auditory intent from the first intent and an active control intent from the second intent. The first intent may be derived from a correlation between the eye movement signal and the head movement signal which is determined by the apparatus as being a natural correlation, as described above, and the second intent may be derived from a correlation between the eye movement signal and the head movement signal which is determined by the apparatus as being an unnatural correlation, as also described above.

Preferably, the apparatus includes and/or is coupled to an electronic media device. Preferably, the apparatus is configured to provide at least one control input, preferably at least one control signal, to control at least one function of the electronic media device based on the determined intent of the user. This may enable the user to control the electronic media device by indicating an intent, such as by naturally or unnaturally moving the eyes relative to the head. This may enhance the user's experience and/or immersion in the content being provided by the media device, e.g., an audio content and/or visual content.

Preferably, the electronic media device may be a consumer electronics device, an entertainment device, e.g., an audio device and/or a visual device and/or a video game device, a therapy device and/or a smart device and/or an Internet of Things (IoT) device and/or any electronic device providing stimulus to the user via one or more of the user's senses, preferably visually and/or acoustically, such as a virtual reality (VR) device and/or an augmented reality (AR) device. Preferably, the electronic media device is configured to generate one or more images which are viewable by the user during normal operation of the apparatus and/or one or more sounds which are audible by the user during normal operation of the apparatus. The above-identified media devices may provide one or more positive effects to the user, such as relaxation and/or an improvement in well-being and/or entertainment. Thus, by enhancing the control of the media device, the effects of the respective media device on the user may not be negatively influenced due to complications with the control of the media device, or the negative influence may at least be reduced versus the prior art.

Preferably, the electronic media device includes at least one sound device configured to generate one or more sounds, preferably music. Preferably, the apparatus is configured to provide at least one control input, preferably at least one control signal, to control at least one function of the sound device based on the determined intent of the user. This may enhance the user's hearing experience, e.g., by urging the user to focus more intensely on the sounds, preferably music, generated by the sound device and/or by enhancing the convenience of the control over the sound device. This may enhance the positive effects the sound device may have on the user, such as relaxation and/or an improvement in well-being and/or entertainment.

Preferably, the electronic media device includes at least one imaging device configured to generate one or more images, preferably moving images, wherein the apparatus is configured to provide at least one control input, preferably at least one control signal, to control at least one function of the imaging device based on the determined intent of the user. This may enhance the user's viewing experience, e.g., by urging the user to focus more intensely on the images, preferably moving images, generated by the imaging device and/or by enhancing the convenience of the control over the imaging device.

This may enhance the positive effects which the imaging device may have on the user, such as relaxation and/or an improvement in well-being and/or entertainment.

Preferably, the apparatus is configured to control at least one of the following functions of the electronic media device: a volume, a light intensity, a 2D or 3D distribution of sound, activation/deactivation of the electronic media device, and a content of the electronic media device. By enabling the user to actively control at least one of the above-identified functions of the electronic media device based on user intent, such as an eye gesture and/or head gesture, the user may conveniently control said functions of the electronic media device. This may enhance the user's experience and/or immersion in the content being provided by the media device, e.g., audio content and/or visual content.

Preferably, the head movement sensing device includes at least one of the following devices configured to sense the head movement signal from the user: at least one accelerometer, at least one orientation sensor, preferably a gyroscope, at least one magnetometer, at least one optical device, and at least one inertial measurement unit (IMU). The above-identified devices may enable the user's head movement to be detected precisely enough to determine a correlation between the user's head movement and the user's eye in a relatively reliable manner and/or accurate manner.

Preferably, the eye movement signal, which can be sensed by the eye movement sensing device, is indicative of at least one horizontal eye movement of the user. Performing horizontal eye movements to indicate a user intent may be intuitive and relatively easy to perform by the user.

Preferably, the apparatus is configured to determine the correlation by comparing:

at least one degree of change in an orientation of the user's head, based on the sensed head movement signal, with a degree of eye movement of the user, based on the sensed eye movement signal, preferably within a certain time frame, preferably a predetermined time frame;

and/or a direction of movement of the user's head, based on the sensed head movement signal, with a direction of eye movement of the user, based on the sensed eye movement signal, preferably within a certain time frame, preferably a predetermined time frame.

Preferably, the apparatus further includes at least one signal amplifier configured to amplify the sensed eye movement signal and/or the sensed head movement signal. This may enhance the ability of the apparatus to process the sensed eye movement signal and/or the sensed head movement signal in order to determine the degree of correlation therebetween.

Preferably, the apparatus is configured to at least partially remove one or more signals, preferably signal artifacts, from the sensed eye movement signal and/or the sensed head movement signal. When sensing signals from the user, e.g., the eye movement signal and/or the head movement signal, one or more sources, such as a muscle movement in a region of the user's body, e.g., the user's jaw and/or neck, may influence the signal which may be undesired and/or detrimental for determining the degree of correlation between the eye movement signal and the head movement signal. By providing a removal of such signals, the eye movement signal and/or the sensed head movement signal may be filtered to increase the ability of determining the degree of correlation between the eye movement signal and the head movement signal.

Preferably, the apparatus is configured to remove at least a portion of an electromyographic signal (EMG), preferably the entire EMG signal, from the sensed eye movement signal, if an EMG signal is present in the sensed eye movement signal. The EMG may originate from muscle activity in the neck, face, jaw and/or other movements which may distort the eye movement signal. The apparatus may be configured to determine if an EMG signal is present in the sensed eye movement signal and, if determined as being present, remove at least a portion of the electromyographic signal (EMG), preferably the entire EMG signal, from the sensed eye movement signal.

Preferably, the apparatus is configured to apply at least one threshold detection algorithm to the sensed eye movement signal to remove the EMG signal. Preferably based on three distinct features, the time-series amplitude of the measured signal between 1 and 5 Hz and 25 and 60 Hz, and lastly the emphasised average amplitude of the fast Fourier transform between 25 and 60 Hz. The emphasis step may include taking the average amplitude between the above-identified frequency and/or frequency ranges to the power of three.

Preferably, the eye movement sensing device is configured to detect at least one electrooculographic (EOG) signal from the user, preferably by being configured to sense an electroencephalographic (EEG) signal and an EOG signal, preferably as a mixed signal including at least the EEG signal and the EOG signal, from the user and extracting the EOG signal, preferably from the sensed mixed signal. Preferably, the eye movement sensing device is configured to sense at least one biopotential signal from the user, preferably by means of at least two electrodes of the eye movement sensing device. The biopotential signal may include at least one EEG signal, at least one EOG signal, and optionally at least one EMG signal and/or further signals related to a biopotential of the user. The apparatus may be configured to extract the EOG signal from the sensed biopotential signal. EOG signals may be relatively reliable and accurate and may therefore provide a relatively reliable and accurate basis for determining user intent via a correlation between the user's head movement and eye movement by means of the apparatus described herein.

Preferably, the apparatus is configured to classify the sensed eye movement into at least one type of eye movement based on the sensed eye movement signal and at least one of the following: determine a direction of eye movement, and determine a degree of change in an orientation of the user's eye relative to a corresponding eye socket of the user and/or relative to a neutral (centered) eye position.

Preferably, the apparatus is configured to determine the type of eye movement by determining:

one or more sequences of maxima and/or minima in the sensed EOG signal, or the sensed EOG signal and the sensed EEG signal;

and/or one or more relative positions of maxima and/or minima in the sensed EOG signal, or the sensed EOG signal and the sensed EEG signal.

For instance, if a first peak is a maximum and followed by a minimum peak, the apparatus may be configured to classify the sensed eye movement as being in a direction to the user's left side. Vice versa, if the first peak is a minimum followed by a maximum, the apparatus may be configured to classify the sensed eye movement as being in a direction to the user's right side.

The object mentioned at the beginning is also solved by a method defined by the features of independent claim 11. The method may determine at least one intent of at least one user by means of an apparatus according to any of the embodiments described herein.

The method may include one or more of the following steps:

sensing at least one eye movement signal from the user by means of at least one eye movement sensing device, the eye movement signal being indicative of at least one eye movement of the user;

sensing at least one head movement signal from the user by means of at least one head movement sensing device, the head movement signal being indicative of at least one head movement of the user;

determining at least one degree of correlation between the eye movement signal and the head movement signal; and determining at least one intent of the user based at least on the determined degree of correlation.

The configurations and advantages described above with respect to the apparatus also apply to the method accordingly.

Preferably, at least one bioelectrical signal, preferably a biopotential signal, preferably an electrooculographic, EOG, signal, is sensed by the eye movement sensing device, the bioelectrical signal being indicative of at least one eye movement of the user.

Preferably, the method further includes the step of classifying the intent of the user by determining whether the determined degree of correlation satisfies at least one criterion.

Preferably, the intent of the user is classified by determining whether the determined correlation is a natural correlation between the sensed eye movement and the sensed head movement of the user or an unnatural correlation between the sensed eye movement and the sensed head movement of the user.

Preferably, a natural correlation between the sensed eye movement and the sensed head movement of the user is determined by determining a threshold for a minimum degree of head movement of the user based on the sensed eye movement of the user and determining if the threshold is reached and/or surpassed by the sensed head movement.

Preferably, a natural correlation between the sensed eye movement and the sensed head movement of the user is determined by determining a direction of head movement of the user and a target direction of head movement of the user based on the sensed eye movement of the user and determining if the determined direction of head movement of the user and the target direction of head movement of the user substantially match and/or are within a target range.

Preferably, a first intent is determined, when the determined correlation satisfies at least one first criterion, and a second intent is determined, when the determined correlation satisfies at least one second criterion, the first criterion differing from the second criterion and/or the first intent differing from the second intent.

Preferably, at least one control input, preferably at least one control signal, is provided by the apparatus to an electronic media device, which is included in or coupled to the apparatus, to control at least one function of the electronic media device based on the determined intent of the user.

Preferably, the method further includes the steps of:

receiving one or more sounds, preferably music, from at least one sound device included in the electronic media device, and controlling at least one function of the sound device based on the determined intent of the user by way of the control input.

Preferably, the method further includes the steps of:

receiving one or more images, preferably moving images, from at least one imaging device included in the electronic media device, and controlling at least one function of the imaging device based on the determined intent of the user by way of the control input.

Preferably, the control input is configured to control at least one of the following functions of the electronic media device: a volume, a light intensity, a 2D or 3D distribution of sound, activation/deactivation of the electronic media device, and a content of the electronic media device.

Preferably, the degree of correlation between the sensed head movement and the sensed eye movement of the user is determined by comparing:

at least one degree of change in an orientation of the user's head, based on the sensed head movement signal, with a degree of eye movement of the user, based on the sensed eye movement signal, preferably within a certain time frame, preferably a predetermined time frame;

and/or a direction of movement of the user's head, based on the sensed head movement signal, with a direction of eye movement of the user, based on the sensed eye movement signal, preferably within a certain time frame, preferably a predetermined time frame.

Preferably, the sensed eye movement signal and/or the sensed head movement signal is amplified by at least one signal amplifier.

Preferably, the method further includes the step of:

at least partially removing one or more signals, preferably signal artifacts, from the sensed eye movement signal and/or the sensed head movement signal.

Preferably, the method further includes the step of:

removing at least a portion of an electromyographic signal, EMG, preferably the entire EMG signal, from the sensed eye movement signal, if an EMG signal is present in the sensed eye movement signal.

Preferably, the EMG signal is removed by applying at least one threshold detection algorithm to the sensed eye movement signal. Preferably, at least one pre-processing step is applied to the sensed eye movement signal, preferably prior to the EMG signal being removed by the threshold detection algorithm. The pre-processing step preferably includes at least one filtering step for at least partially filtering the sensed eye movement signal, e.g., by filtering one or more artifacts from the sensed eye movement signal.

The object mentioned at the beginning is also solved by a computer program. The computer program comprises instructions which, when the program is executed by a computer, cause the computer to carry out the steps of the method of any one of the embodiments described herein.

The configurations and advantages described above with respect to the apparatus and/or the method also apply to the computer program accordingly.

The object mentioned at the beginning is also solved by a computer program product. The computer program product comprises instructions which, when the program is executed by a computer, cause the computer to carry out the steps of the method of any one of the embodiments described herein.

The configurations and advantages described above with respect to the apparatus and/or the method also apply to the computer program product accordingly.

The following list of aspects may provide alternative and/or further features of the invention:

1. An apparatus for determining at least one intent of at least one user, the apparatus including: at least one first sensing device, preferably an eye movement sensing device, configured to sense at least one first signal from the user, the first signal being indicative of at least one movement of a first body part of the user, preferably least one eye movement of the user;

at least one second sensing device, preferably a head movement sensing device, configured to sense at least one second signal from the user, the second signal being indicative of at least one movement of a second body part of the user, preferably at least one head movement of the user, the first body part differing from the second body part;

wherein the apparatus is configured to determine at least one degree of correlation between the first signal and the second signal, wherein the apparatus is configured to determine at least one intent of the user based at least on the determined degree of correlation.

2. The apparatus according to aspect 1, wherein the apparatus is configured to be wearable on at least a portion of the user's body, preferably at least partially on the user's head and/or neck.

3. The apparatus according to aspect 1 or 2, wherein the first sensing device, preferably the eye movement sensing device, is configured to sense at least one bioelectrical signal, preferably a biopotential signal, preferably an electrooculographic (EOG) signal, from the user, the bioelectrical signal being indicative of the at least one eye movement of the user.

4. The apparatus according to any of the preceding aspects, wherein the first sensing device includes at least one sensor region, preferably including at least two electrodes, made at least partially of an electrically conductive material.

5. The apparatus according to aspect 4, wherein at least a portion of the first sensing device, preferably the eye movement sensing device, is configured to be inserted at least partially into a cavity of the user's ear such that the sensor region contacts at least a portion of the user's ear anatomy within the cavity.

6. The apparatus according to any of the preceding aspects, wherein the first sensing device, preferably the eye movement sensing device, includes at least two sensing components, preferably eye movement sensing components, each having at least one sensor region, preferably including at least two electrodes, made at least partially of an electrically conductive material.

7. The apparatus according to aspect 6, wherein at least a portion of each sensing component is configured to be inserted at least partially into a cavity of one of the user's ears, respectively, such that the respective sensor region contacts at least a portion of the user's ear anatomy within the respective cavity.

8. The apparatus according to aspect 6 or 7, wherein the sensing components are communicatively interconnected.

9. The apparatus according to any of the preceding aspects, including at least one earpiece configured to be worn on the user's ear(s) and/or over the user's ear(s) and/or at least partially within a cavity of the user's ear(s), wherein the earpiece includes at least the first sensing device, preferably the eye movement sensing device, and/or the second sensing device, preferably the head movement sensing device.

10. The apparatus according to aspect 9, wherein the earpiece includes at least one eartip configured to be inserted at least partially into a cavity of the user's ear, wherein the eartip includes at least the first sensing device, preferably the eye movement sensing device, wherein the eartip is configured such that the first sensing device is at least partially inserted into the cavity of the user's ear, when the eartip is inserted at least partially into the cavity of the user's ear.

11. The apparatus according to any of the preceding aspects, including at least one earbud configured to be inserted at least partially into a cavity of the user's ear, wherein the earbud includes at least the first sensing device and/or the second sensing device.

12. The apparatus according to any of the preceding aspects, wherein the apparatus is configured to classify the intent of the user by determining whether the determined degree of correlation satisfies at least one criterion.

13. The apparatus according to aspect 12, wherein the apparatus is configured to determine whether the determined correlation is a natural correlation between the sensed movement of the first body part of the user and the sensed movement of the second body part of the user or an unnatural correlation between the sensed movement of the first body part of the user and the sensed movement of the second body part of the user according to at least one criterion to classify the intent of the user based thereon.

14. The apparatus according to any of the preceding aspects, wherein the apparatus is configured to determine a natural correlation between the sensed movement of the first body part of the user and the sensed movement of the second body part of the user by determining a threshold for a minimum degree of movement of the second body part of the user based on the sensed movement of the first body part of the user and determining if the threshold is reached and/or surpassed by the sensed movement of the second body part of the user.

15. The apparatus according to any of the preceding aspects, wherein the apparatus is configured to determine a natural correlation between the sensed movement of the first body part and the sensed movement of the second body part of the user by determining a direction of movement of the second body part of the user and a target direction of movement of the second body part of the user based on the sensed movement of the first body part of the user and determining if the determined direction of movement of the second body part of the user and the target direction of movement of the second body part of the user substantially match and/or are within a target range.

16. The apparatus according to any of the preceding aspects, wherein the apparatus is configured to determine a first intent, when the determined correlation satisfies at least one first criterion, and a second intent, when the determined correlation satisfies at least one second criterion, the first criterion differing from the second criterion and/or the first intent differing from the second intent.

17. The apparatus according to any of the preceding aspects, wherein the apparatus includes and/or is coupled to an electronic media device, wherein the apparatus is configured to provide at least one control input, preferably at least one control signal, to control at least one function of the electronic media device based on the determined intent of the user.

18. The apparatus according to aspect 17, wherein the electronic media device includes at least one sound device configured to generate one or more sounds, preferably music, wherein the apparatus is configured to provide at least one control input, preferably at least one control signal, to control at least one function of the sound device based on the determined intent of the user.

19. The apparatus according to aspect 17 or 18, wherein the electronic media device includes at least one imaging device configured to generate one or more images, preferably moving images, wherein the apparatus is configured to provide at least one control input, preferably at least one control signal, to control at least one function of the imaging device based on the determined intent of the user.

20. The apparatus according to any of aspects 17 to 19, wherein the apparatus is configured to control at least one of the following functions of the electronic media device and/or of at least one further device, such as a smart device and/or an internet of things (IoT) device: a volume, a light intensity, a 2D or 3D distribution of sound, activation/deactivation of the electronic media device, and a content of the electronic media device.

21. The apparatus according to any of the preceding aspects, wherein the second sensing device includes at least one of the following devices configured to sense the second signal from the user: at least one accelerometer, at least one orientation sensor, preferably a gyroscope, at least one magnetometer, at least one optical device, and at least one inertial measurement unit (IMU).

22. The apparatus according to any of the preceding aspects, wherein the first signal, which can be sensed by the first sensing device, is indicative of at least one horizontal eye movement of the user.

23. The apparatus according to any of the preceding aspects, wherein the apparatus is configured to determine the correlation by comparing:
at least one degree of change in an orientation of the second body part, based on the sensed second signal, with a degree of movement of the first body part of the user, based on the sensed first signal, preferably within a certain time frame, preferably a predetermined time frame;
and/or
a direction of movement of the second body part, based on the sensed second signal, with a direction of movement of the first body part, based on the sensed first signal, preferably within a certain time frame, preferably a predetermined time frame.

24. The apparatus according to any of the preceding aspects, further including at least one signal amplifier configured to amplify the sensed first signal and/or the sensed second signal.

25. The apparatus according to any of the preceding aspects, wherein the apparatus is configured to at least partially remove one or more signals, preferably signal artifacts, from the sensed first signal and/or the sensed second signal.

26. The apparatus according to any of the preceding aspects, wherein the apparatus is configured to remove at least a portion of an electromyographic signal (EMG), preferably the entire EMG signal, from the sensed first signal, if an EMG signal is present in the sensed first signal.

27. The apparatus according to aspect 26, wherein the apparatus is configured to apply at least one threshold detection algorithm to the sensed first signal to remove the EMG signal.

28. The apparatus according to any of the preceding aspects, wherein the first sensing device is configured to detect at least one electrooculographic (EOG) signal from the user, preferably by being configured to sense an electroencephalographic (EEG) and an EOG signal from the user, preferably as a mixed signal including at least the EEG signal and the EOG signal, and extracting the EOG signal, preferably from the sensed mixed signal.

29. The apparatus according to any of the preceding aspects, wherein the apparatus is configured to classify the sensed movement of the first body part into at least one type of movement of the first body part based on the sensed first signal and at least one of the following: determine a direction of movement of the first body part, and determine a degree of change in an orientation of the second body part relative to a further body part of the user, preferably a corresponding eye socket of the user.

30. The apparatus according to aspect 29, wherein the apparatus is configured to determine the type of movement of the first body part by determining:
one or more sequences of maxima and/or minima in the sensed EOG signal, or the sensed EOG signal and the sensed EEG signal;
and/or
one or more relative positions of maxima and/or minima in the sensed EOG signal, or the sensed EOG signal and the sensed EEG signal.

31. A method for determining at least one intent of at least one user by means of an apparatus according to any of the preceding aspects, the method including the following steps:
sensing at least one first signal from the user by means of at least one first sensing device, the first signal being indicative of at least one movement of a first body part of the user;
sensing at least one second signal from the user by means of at least one second sensing device, the second signal being indicative of at least one movement of a second body part of the user, the first body part differing from the second body part;
determining at least one degree of correlation between the first signal and the second signal; and
determining at least one intent of the user based at least on the determined degree of correlation.

32. The method according to aspect 31, wherein at least one bioelectrical signal, preferably a biopotential signal, preferably an electrooculographic, EOG, signal, is sensed by the first sensing device, the bioelectrical signal being indicative of at least one movement of the first body part.

33. The method according to aspect 31 or 32, further including the step of:
classifying the intent of the user by determining whether the determined degree of correlation satisfies at least one criterion.

34. The method according to aspect 33, wherein the intent of the user is classified by determining whether the determined correlation is a natural correlation between the sensed movement of the first body part and the sensed movement of the second body part or an unnatural correlation between the sensed movement of the first body part and the sensed movement of the second body part.

35. The method according to aspect 33 or 34, wherein a natural correlation between the sensed movement of the first body part and the sensed movement of the second body part is determined by determining a threshold for a minimum degree of movement of the second body part based on the sensed movement of the first body part and determining if the threshold is reached and/or surpassed by the sensed movement of the second body part.

36. The method according to any of aspects 33 to 35, wherein a natural correlation between the sensed movement of the first body part and the sensed movement of the second body part is determined by determining a direction of movement of the second body part and a target direction of movement of the second body part based on the sensed movement of the first body part and determining if the determined direction of movement of the second body part and the target direction of movement of the second body part substantially match and/or are within a target range.

37. The method according to any of aspects 31 to 36, wherein a first intent is determined, when the determined correlation satisfies at least one first criterion, and a second intent is determined, when the determined correlation satisfies at least one second criterion, the first criterion differing from the second criterion and/or the first intent differing from the second intent.

38. The method according to any of aspects 31 to 37, wherein at least one control input, preferably at least one control signal, is provided by the apparatus to an electronic media device, which is included in or coupled to the apparatus, to control at least one function of the electronic media device based on the determined intent of the user.

39. The method according to aspect 38, further including the steps of:
receiving one or more sounds, preferably music, from at least one sound device included in the electronic media device, and
controlling at least one function of the sound device based on the determined intent of the user by way of the control input.

40. The method according to aspect 38 or 39, further including the steps of:
receiving one or more images, preferably moving images, from at least one imaging device included in the electronic media device, and
controlling at least one function of the imaging device based on the determined intent of the user by way of the control input.

41. The method according to any of aspects 38 to 40, wherein the control input is configured to control at least one of the following functions of the electronic media device: a volume, a light intensity, a 2D or 3D distribution of sound, activation/deactivation of the electronic media device, and a content of the electronic media device.

42. The method according to any of aspects 31 to 41, wherein the degree of correlation between the sensed movement of the second body part and the sensed movement of the first body part is determined by comparing:
at least one degree of change in an orientation of the second body part, based on the sensed second signal, with a degree of movement of the first body part, based on the sensed first signal, preferably within a certain time frame, preferably a predetermined time frame; and/or
a direction of movement of the second body part, based on the sensed second signal, with a direction of movement of the first body part, based on the sensed first signal, preferably within a certain time frame, preferably a predetermined time frame.

43. The method according to any of aspects 31 to 42, wherein the sensed second signal and/or the sensed first signal is amplified by at least one signal amplifier.

44. The method according to any of aspects 31 to 43, further including the step of:
at least partially removing one or more signals, preferably signal artifacts, from the sensed first signal and/or the sensed second signal.

45. The method according to any of aspects 31 to 44, further including the step of:
removing at least a portion of an electromyographic signal, EMG, preferably the entire EMG signal, from the sensed first signal, if an EMG signal is present in the sensed first signal.

46. The method according to aspect 45, wherein the EMG signal is removed by applying at least one threshold detection algorithm to the sensed first signal.

47. Computer program comprising instructions which, when the program is executed by a computer, cause the computer to carry out the steps of the method of any one of aspects 31 to 46.

48. Computer program product comprising instructions which, when the program is executed by a computer, cause the computer to carry out the steps of the method of any one of aspects 31 to 46.

The exemplary embodiments disclosed herein are directed to providing features that will become readily apparent by reference to the following description when taken in conjunction with the accompany drawings. In accordance with various embodiments, exemplary systems, methods, devices and computer program products are disclosed herein. It is understood, however, that these embodiments are presented by way of example and not limitation, and it will be apparent to those of ordinary skill in the art who read the present disclosure that various modifications to the disclosed embodiments can be made while remaining within the scope of the present disclosure.

Thus, the present disclosure is not limited to the exemplary embodiments and applications described and illustrated herein. Additionally, the specific order and/or hierarchy of steps in the methods disclosed herein are merely exemplary approaches. Based upon design preferences, the specific order or hierarchy of steps of the disclosed methods or processes can be re-arranged while remaining within the scope of the present disclosure. Thus, those of ordinary skill in the art will understand that the methods and techniques disclosed herein present various steps or acts in a sample order, and the present disclosure is not limited to the specific order or hierarchy presented unless expressly stated otherwise.

Preferred embodiments of the present invention are further elucidated below with reference to the figures. The described embodiments do not limit the present invention.

FIG. 6 shows a schematic diagram of a method according to an embodiment of the present disclosure;

Figures 1, 2:
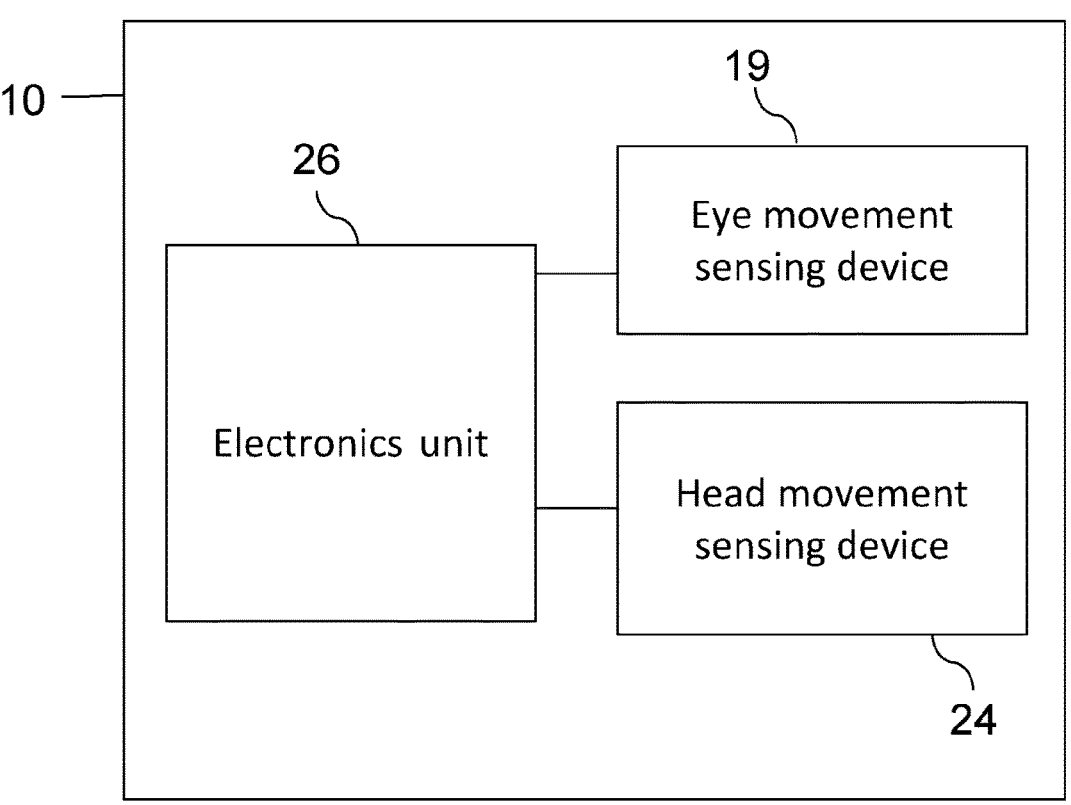
FIG. 1 shows, in a schematic view, an apparatus for determining an intent of a user according to an embodiment of the present disclosure
FIG. 2 shows, in a schematic perspective view, an apparatus for determining an intent of a user according to an embodiment of the present disclosure.

FIG. 1 shows an apparatus 10 for determining at least one intent of at least one user. The apparatus 10 includes an at least one eye movement sensing device 19 and at least one head movement sensing device 24. The apparatus 10 preferably further includes an electronics unit 26, which may include a processing unit.

The at least one eye movement sensing device 19 is configured to sense at least one eye movement signal from the user, the eye movement signal being indicative of at least one eye movement of the user.

The at least one head movement sensing device 24 is configured to sense at least one head movement signal from the user, the head movement signal being indicative of at least one head movement of the user.

The apparatus 10 is configured to determine at least one degree of correlation between the eye movement signal and the head movement signal, wherein the apparatus 10 is configured to determine at least one intent of the user based at least on the determined degree of correlation.

Alternatively, the electronics unit 26 or the processing unit thereof may be configured to determine at least one degree of correlation between the eye movement signal and the head movement signal, wherein the apparatus 10 is configured to determine at least one intent of the user based at least on the determined degree of correlation.

As outlined herein, the electronics unit 26 and/or the processing unit may also be provided as external devices and may thus not be part of the apparatus 10.

FIG. 2 shows an apparatus 10 for determining at least one intent of at least one user according to another embodiment. The apparatus 10 includes two earpieces 12, 14 configured to be worn on the user's ears and/or over at least a portion of the user's ears and/or at least partially within a cavity, such as an ear canal and/or concha, of the user's ears. Each earpiece 12, 14 includes an eartip 16, 18, which is preferably removable from a section of the respective earpiece 12, 14, configured to be inserted at least partially into the respective cavity of the user's ears.

The apparatus 10 further includes an eye movement sensing device 19 configured to sense at least one eye movement signal from the user, wherein each earpiece 12, 14 includes an eye movement sensing component 20, 22 of the eye movement sensing device 19.

Each eye movement sensing component 20, 22 of the eye movement sensing device 19 may include at least one sensor region, preferably including at least two electrodes, made at least partially of an electrically conductive material. Preferably, the eye movement sensing components 20, 22 are manoeuvrable relative to each other. Thus, each eye movement sensing component 20, 22 may be positioned separately in the respective cavity of the user's ears, i.e., by positioning one eye movement sensing component 20 on the user's first ear and positioning the other eye movement sensing component 22 on the user's second ear.

The eye movement signal sensed by the eye movement sensing device 19 may be indicative of at least one eye movement of the user. The sensor region(s) of the eye movement sensing components 20, 22 may be integrated at least partially in the respective eartip 16, 18 of the respective earpiece 12, 14 such that the sensor region(s) of the eye movement sensing component 20, 22 is/are at least partially inserted into the cavity of the user's ear, respectively, when the respective eartip 16, 18 is inserted at least partially into the cavity of the user's ear, respectively.

The eye movement sensing device 19 is preferably configured to sense a bioelectrical signal, preferably a biopotential signal, preferably an electroencephalographic (EEG) signal and/or an electrooculographic signal (EOG). Preferably, the eye movement sensing device 19 is configured to detect at least one EOG signal from the user, preferably by being configured to sense an EEG signal and an EOG signal, preferably as a mixed signal including at least the EEG signal and the EOG signal, from the user and extracting the EOG signal, preferably from the sensed mixed signal. Preferably, the eye movement sensing device 19 is configured to sense at least one biopotential signal from the user, preferably by means of at least two electrodes of the eye movement sensing device 19. The biopotential signal may include at least one EEG signal, at least one EOG signal, and optionally at least one EMG signal and/or further signals related to a biopotential of the user. The apparatus 10 may be configured to extract the EOG signal from the sensed biopotential signal. However, the eye movement sensing device 19 may be configured to sense any physiological signal from the user which may be indicative of an eye movement of the user.

The apparatus 10 further includes a head movement sensing device 24 configured to sense at least one head movement signal from the user. The head movement signal may be indicative of at least one head movement of the user. As shown in FIG. 2, the head movement sensing device 24 may be mounted to an earpiece of the apparatus, such as the earpiece 14 as shown in FIG. 2. Alternatively, the head movement sensing device 24 may be attached to a different section of the apparatus 10 or the head movement sensing device 24 may be mountable to the user's body independently from the other components of the apparatus 10, e.g., via an attachment device, such as a clip or suction cup. The apparatus 10 may include a plurality of head movement sensing devices 24, e.g., with at least one head movement sensing device 24 attached to each earpiece 12, 14.

The head movement sensing device 24 preferably includes at least one of the following devices configured to sense the user's head movement: at least one accelerometer, at last one gyroscope, at least one magnetometer, at least one inertial measurement unit (IMU), at least one optical sensor, e.g., a camera, at least one infrared sensor, preferably a passive infrared sensor, and at least one microwave sensor. However, the head movement sensing device 24 may include any device capable of sensing a signal from the user which is indicative of a head movement of the user.

The apparatus 10 may be configured to determine at least one degree, preferably a plurality of degrees, of correlation between the eye movement signal sensed by the eye movement sensing device 20, 22 and the head movement signal sensed by the head movement sensing device 24.

The apparatus 10 may further be configured to determine at least one intent of the user based at least on the determined degree of correlation.

The apparatus 10 shown in FIG. 2 further includes an electronics unit 26. The electronics unit 26 may include at least one processing unit for processing the eye movement signal and/or the head movement signal. Alternatively, or additionally, data relating to the eye movement signal and/or the head movement signal may be provided to an external processing unit, such as an external evaluating device.

The electronics unit 26 may further include a storage means for storing data relating to the eye movement signal and/or the head movement signal and/or to the determined correlation between the eye movement signal and/or the head movement signal and/or one or more user intents and/or one or more criteria for determining the correlation between the eye movement signal and/or the head movement signal and/or one or more criteria for determining user intent. The electronics unit 26 may be connectable to a power source, such as one or more batteries, preferably rechargeable batteries, for providing power. The electronics unit 26 may include at least one internal power storage, preferably one or more batteries, preferably rechargeable batteries, for providing power to the apparatus 10.

The electronics unit 26 may further include at least one amplifier, preferably an analog front-end amplifier, for amplifying the eye movement signal and/or the head movement signal. The electronics unit 26 may also include at least one filter device, for filtering the eye movement signal and/or the head movement signal, e.g., to remove one or more artifacts from the eye movement signal and/or the head movement signal. Preferably, the filter device, i.e., at least one filtering function, is implemented as, e.g. by a processor and optionally a data storage (memory device) provided in the electronics unit 26, and/or on an external device capable of running software, e.g., a smart device, such as a smartphone, etc. In the latter case, the filter device and the amplifier are preferably separate. Alternatively, or additionally, at least one of the earpieces 12, 14 may be configured to run the software. For this purpose, at least one of the earpieces 12, 14 may include a processing device, and optionally also a data storage (memory device). Preferably, the electronics unit 26 may be integrated in at least one of the earpieces 12, 14. The filter device may also be a separate hardware component and/or a combination of hardware components and software functions.

The electronics unit 26 may further include a transmitting device configured to transmit data, such as data related to the eye movement signal and/or the head movement signal, to an external device, such a personal device of the user, e.g., a smartwatch and/or smartphone, or a server or cloud. For this purpose, the transmitting device may be configured to provide a connection, preferably a wireless connection, e.g., a Bluetooth connection, to the external device. The external device may be configured to evaluate and/or process the received data.

As shown in FIG. 2, the electronics unit 26 may be connected to the earpieces 12, 14 via cables 28, 30. Alternatively, the electronics unit 26 may be connected to the earpieces 12, 14 wirelessly, e.g., via a Bluetooth connection and/or a Wifi connection.

The electronics unit 26 may be configured to perform signal processing and/or signal interpretation, e.g., to the eye movement signal and/or the head movement signal, using heuristics and/or machine learning. Instead of being a separate component, as shown in FIG. 2, the electronics unit 26 may be integrated in at least one of the earpieces 12, 14.

The apparatus 10 may be couplable to an electronic media device (not shown), such as an imaging device, e.g., a tablet, smartphone, television or a video game device, and/or an audio device, such as a tablet, smartphone or a video game device. Preferably, the earpieces 12, 14 may include at least one audio driver and/or audio speaker for generating one or more sounds, preferably music and/or speech, and providing the sounds to the user's ears. Preferably, the electronic media device and the apparatus 10 are communicatively couplable to each to transmit audio signals from the electronic media device to the earpieces 12, 14 such that the audio driver and/or audio speaker of the earpieces 12, 14 output(s) the sound of the electronic media device to the user. The apparatus 10 may also include a screen (not shown) to output one or more images from the electronic media device.

Figure 3:
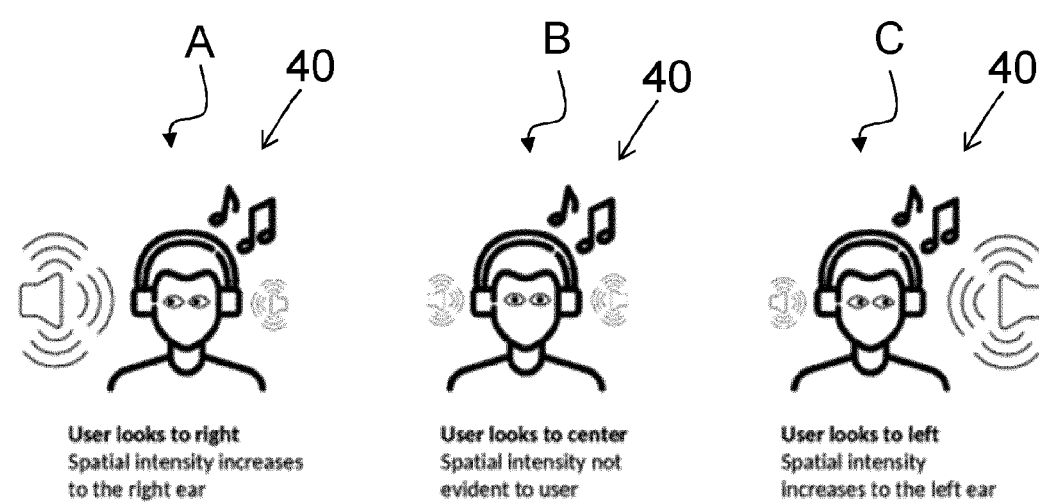
FIG. 3 shows, in a schematic illustration, exemplary events which are detectable by the apparatus shown in FIG. 1 or 2.

FIG. 3 shows, in a schematic illustration, exemplary events of user intent which are detectable by the apparatus 10 shown in FIG. 1 or 2. In particular, FIG. 3 shows a user 40 in three different user situations A, B and C. In each user situation, the user 40 is depicted wearing headphones which provide audio to the user's ears. The headphones are only depicted for symbolic purposes. The audio may be provided by the earpieces 12, 14 of the apparatus 10, which for this purpose may include at least one audio driver and/or audio speaker for generating one or more sounds, preferably music and/or speech. The apparatus 10 may also include a screen (not shown) to output one or more images.

The apparatus 10 may be configured to control and/or alter a spatial distribution or spatial variance of one or more properties of the audio provided to the user 40. For this purpose, the apparatus 10 may be communicatively coupled to an electronic media device (not shown), such as a tablet, a video game device, a smartphone, a television, a radio, etc. The three user situations A, B and C show different spatial distributions of intensity of the audio provided to the user 40, as indicated by a symbol of a loudspeaker to the left-side and right-side of the user 40 in various sizes. A larger sized loudspeaker indicates a higher intensity of the audio provided to the user 40 and a smaller sized loudspeaker indicates a lower intensity of the audio provided to the user 40.

On the left-hand side of FIG. 3, user situation A is depicted in which the user maintains a neutral head position, i.e., a centered head position with no or only minimal movement. The user also moves the eyes to the right side, from the perspective of the user in FIG. 3. The relation between the neutral head position and the movement of the user's eyes to the right may be considered as not corresponding to a natural head-eye movement behaviour of the user. Thus, such a determined correlation between the eye movement signal and the head movement signal may be interpreted/determined by the apparatus 10, e.g., the electronics unit 26 or an external evaluating/processing unit, as one type or class of unnatural correlation. The apparatus 10 may be configured to interpret such an unnatural correlation between the eye movement signal and the head movement signal as a user intent for achieving one or more effects, such as controlling one or more functions of the electronic media device. As shown in FIG. 3, such a determined correlation between the eye movement signal and the head movement signal of the user may be utilized to provide one or more control signals to adjust the intensity of the audio provided to the user. For instance, as shown in FIG. 3, the depicted relation between the neutral head position and the movement of the user's eyes to the right may trigger the intensity of the audio to be increased to the user's right ear In the center of FIG. 3, user situation B is depicted in which the user maintains a substantially neutral head position, i.e., a centered head position with no or only minimal movement, and a substantially neutral eye position, i.e., a centered eye position with no or only minimal movement. The relation between the neutral head position and the neutral eye position of the user may be considered as corresponding to a natural head-eye movement behaviour of the user. Thus, such a determined correlation between the eye movement signal and the head movement signal may be interpreted/determined by the apparatus 10, e.g., the electronics unit 26 or an external evaluating/processing unit, as a natural correlation. The apparatus 10 may be configured to interpret such a natural correlation between the eye movement signal and the head movement signal as not being a user intent. Thus, the apparatus 10 may not provide any control signals to the electronic media device based on the determined correlation between the eye movement signal and the head movement signal of the user.

On the right-hand side of FIG. 3, user situation C is depicted in which the user maintains a substantially neutral head position, i.e., a centered head position with no or only minimal movement. The user moves the eyes to the left side, from the perspective of the user in FIG. 3. The relation between the neutral head position and the movement of the user's eyes to the left may be considered as not corresponding to a natural head-eye movement behaviour of the user. Thus, such a determined correlation between the eye movement signal and the head movement signal may be interpreted/determined by the apparatus 10, e.g., the electronics unit 26 or an external evaluating/processing unit, as one type or class of an unnatural correlation, e.g., a different type or class of unnatural correlation compared with user situation A. The apparatus 10 may be configured to interpret such an unnatural correlation between the eye movement signal and the head movement signal as a user intent for increasing the intensity on the user's left side via one or more control signals for adjusting the intensity of the audio provided to the user, as shown in user situation C in FIG. 3.

Figure 4:
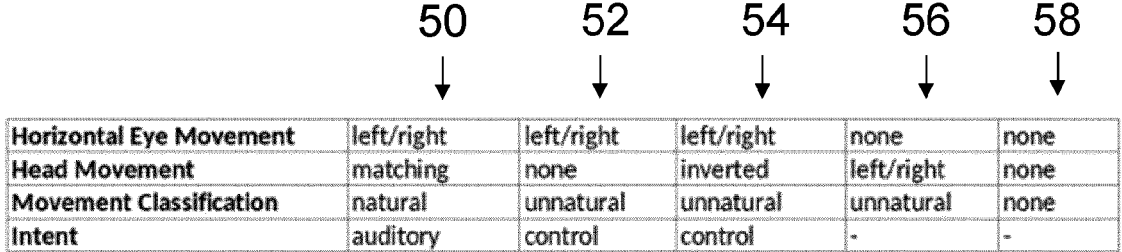
FIG. 4 shows, in a table, exemplary classifications of user intent performed by the apparatus shown in FIG. 1 or 2.

FIG. 4 shows a table with different exemplary classifications 50 to 58 of user intent performed by the apparatus 10 arranged in columns of the table of FIG. 4. According to classification 50, the apparatus 10 determines that a sensed horizontal eye movement of the user, by means of the eye movement sensing device 19, to the left side or right side of the user 40 paired with a sensed head movement, by means of the head movement sensing device 24, in the same direction as the sensed eye movement, i.e., to the left side or right side of the user 40, respectively, corresponds to a first type or class of natural correlation between the sensed eye movement and the sensed head movement of the user 40. Thus, the apparatus 10 determines the movement classification of the classification 50 as a natural movement classification. The apparatus 10 is configured to interpret the movement combination shown in classification 50 as an auditory intent and/or visual intent and/or haptic intent of the user, i.e., what the user wants to sense, i.e., hear and/or see and/or feel. Thus, the user's intent according to classification 50 may be utilized to adjust the corresponding media device.

According to classification 52, the apparatus 10 determines that a sensed horizontal eye movement of the user to the left side or right side of the user 40 paired with a neutral head position, i.e., no or only minimal head movement, sensed by the head movement sensing device 24, corresponds to a second type or class of unnatural correlation between the sensed eye movement and the sensed head movement of the user 40. The apparatus 10 is configured to interpret the movement combination shown in classification 52 as an active control intent, e.g. the user wants to change a scene or change the volume of the audio. Thus, the user's intent according to classification 52 may be utilized to, e.g., actively change the scene or volume of the audio.

According to classification 54, the apparatus 10 determines that a sensed horizontal eye movement of the user to the left side or right side of the user 40 paired with an inverted head movement, i.e., a head movement which is in a direction which is substantially opposite to a direction of the user's eye movement, corresponds to a third type or class of unnatural correlation between the sensed eye movement and the sensed head movement of the user 40. The apparatus 10 is configured to interpret the movement combination shown in classification 54 as an active control intent, preferably a different active control intent compared with the active control intent indicated in classification 52.

Classification 56 shows that no horizontal eye movement of the user paired with a head movement of the user to the left or right also corresponds to an unnatural correlation between the sensed eye movement and the sensed head movement of the user 40. Thus, the apparatus 10 determines the movement classification of the classification 52 as an unnatural movement classification. However, in contrast to classifications 50 to 54, the apparatus 10 is configured to interpret the movement combination shown in classification 56 as not relating to a user intent. Thus, classification 56 may not be utilized to control one or more functions of the electronic media device.

Finally, classification 58 shows that no horizontal eye movement of the user paired with no head movement of the user is also interpreted as not relating to a user intent. Thus, no user intent may be derived from classification 58.

Figure 5:
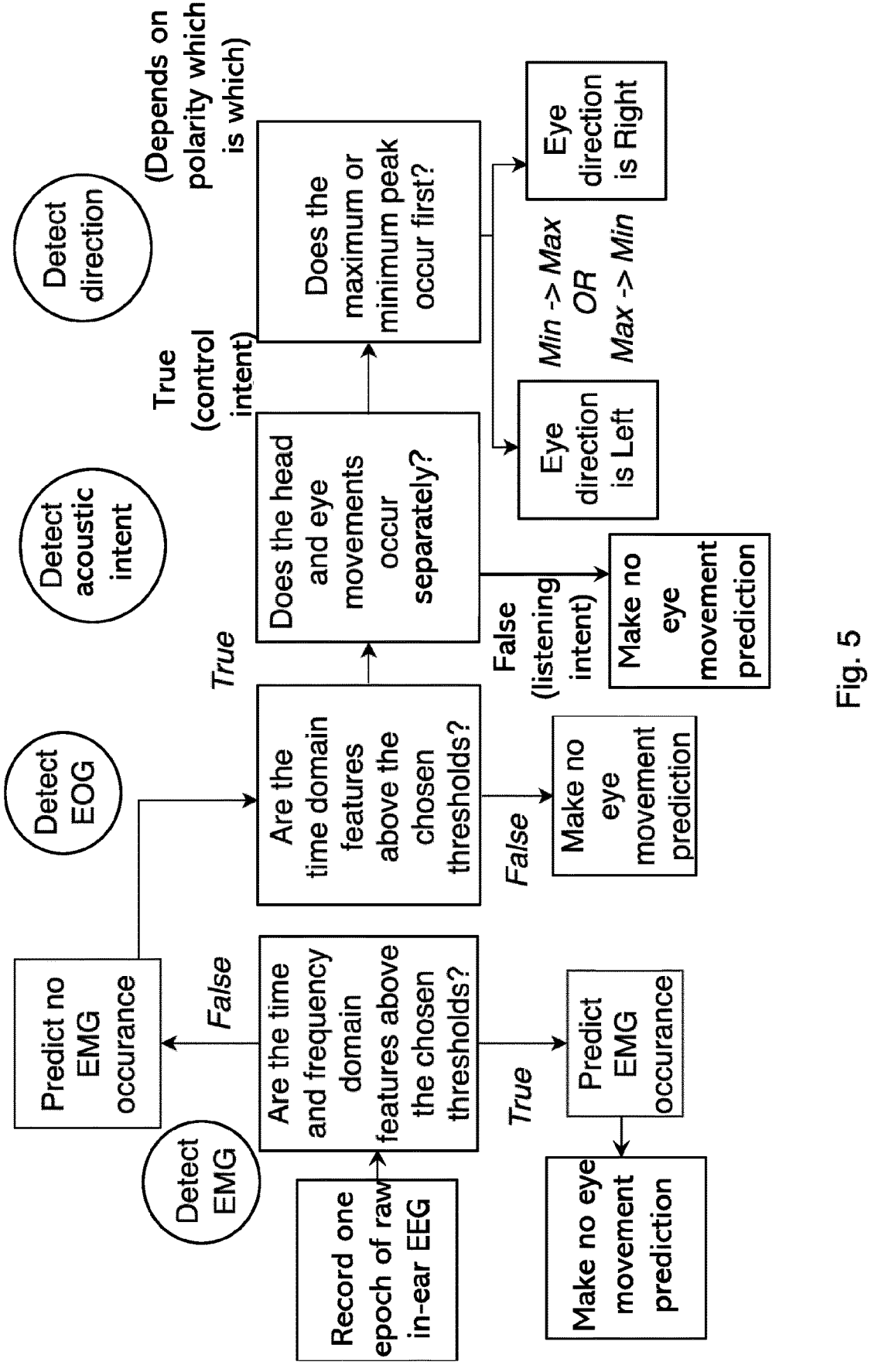
FIG. 5 shows a schematic flow chart for determining user intent by means of the apparatus shown in FIG. 1 or 2.

FIG. 5 shows, in a schematic illustration, a flow chart for determining user intent by means of the apparatus 10. First, the apparatus 10 records at least one raw biopotential/bioelectrical signal from the user by means of the eye movement sensing device 19.

The biopotential/bioelectrical signal may include at least one EEG signal, at least one EOG signal, and optionally at least one EMG and/or further signals related to a biopotential of the user.

Next, the apparatus 10 detects whether the biopotential/bioelectrical signal contains, e.g., is contaminated by, an electromyographic (EMG) signal by determining if the respective time and frequency domain features of the detected biopotential/bioelectrical signal are above one or more chosen, preferably predetermined, thresholds. If the answer is "True", the apparatus 10 predicts that an EMG signal is present in the biopotential/bioelectrical signal and makes no eye movement prediction due to the presence of said EMG signal. If the answer is "False", the apparatus 10 does not predict that an EMG signal is present in the sensed biopotential/bioelectrical signal.

If the answer in the above-identified step is "False", subsequently, the apparatus 10 detects an electrooculographic (EOG) signal from the biopotential/bioelectrical signal. First, the apparatus 10 determines if the respective time domain features of the sensed biopotential/bioelectrical signal are above one or more chosen, preferably predetermined, thresholds. If the answer is "False", the apparatus 10 does not make an eye movement prediction. If the answer is "True", the apparatus 10 determines if the sensed head movement and the sensed eye movement occur separately, i.e., if the sensed head movement naturally correlates with the sensed eye movement, e.g., if the sensed head movement follows the sensed eye movement within a certain, preferably predetermined, time frame. If the answer is "False", the apparatus 10 does not make an eye movement prediction and the user intent is classified as a "listening intent". If the answer is "True", the apparatus 10 classifies the user intent as a "control intent".

Thereafter, if the answer in the above-identified step is "True", the apparatus 10 determines if a maximum peak or a minimum peak occurs first in the sensed biopotential/bioelectrical signal. If a minimum peak occurs first, preferably followed by a maximum peak, the apparatus 10 may determine that the direction of the sensed eye movement is to the right side of the user. If a maximum peak occurs first, preferably followed by a minimum peak, the apparatus 10 may determine that the direction of the sensed eye movement is to the left side of the user.

A correlation between the determined eye movement and the head movement of the user may then be determined to determine and/or classify an intent of the user.

Instead of, or in addition to, controlling or altering the spatial variance of one or more properties of the audio, e.g., a distribution of the intensity of the audio provided to the user as shown in FIG. 5 and described above, the apparatus 10 described herein may also be configured to provide, or at least trigger, one or more control inputs, e.g., control signals, based on the determined user intent to control one or more functions of any electronic device. For instance, the determined user intent may be utilized to trigger one or more control inputs to alter one or more functions of a visual device, i.e., a device configured to generate one or more images, such as by changing the scene displayed by the visual device. In another, non-limiting example, the determined user intent may be utilized to trigger one or more control inputs to alter one or more functions of a lighting device, such as a light intensity and/or an activation/deactivation of the light device, and/or a video game device.

FIG. 6 shows a schematic diagram of a method according to an embodiment of the present disclosure. The method may be used for determining at least one intent of at least one user by means of an apparatus of any of the embodiments described above. The method comprises the following steps:

S100: sensing at least one eye movement signal from the user by means of at least one eye movement sensing device.

S110: sensing at least one head movement signal from the user by means of at least one head movement sensing device.

S120: determining at least one degree of correlation between the eye movement signal and the head movement signal.

S130: determining at least one intent of the user based at least on the determined degree of correlation.

The steps S100 and S110 may be performed simultaneously or sequentially or at least partially simultaneously, i.e., in a partial overlapping manner. The steps S100 and S110 may be performed in any order, i.e., the step S100 may be performed, or at least started, before the step S110 or vice versa.

The eye movement signal may be indicative of at least one eye movement of the user.

The head movement signal may be indicative of at least one head movement of the user.

Figure 7:
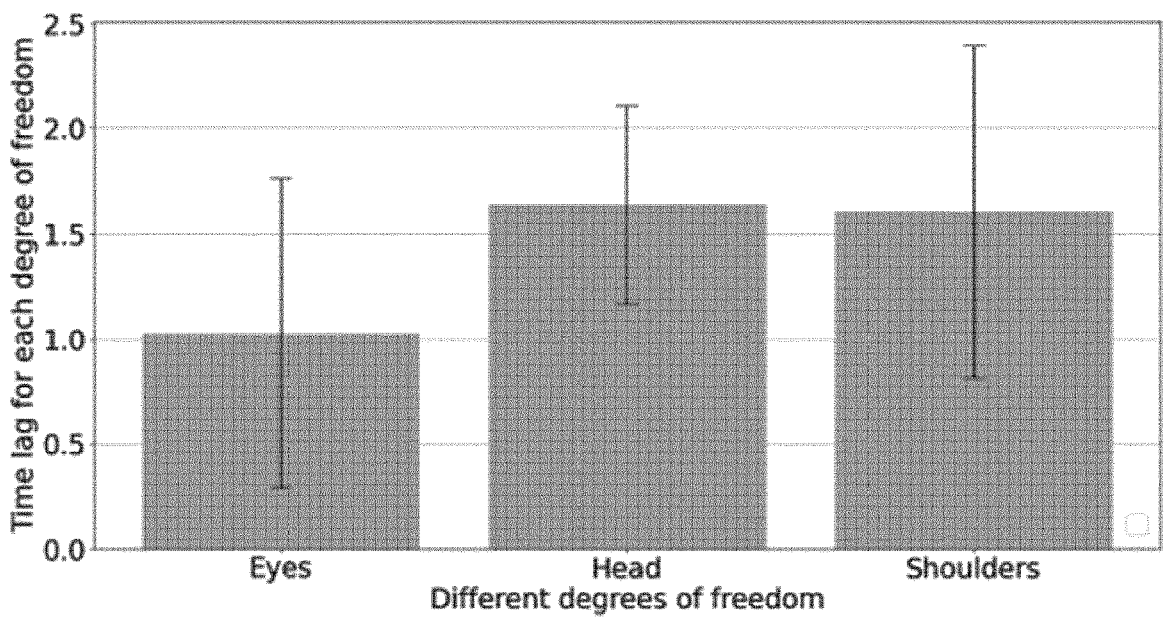
FIG. 7 shows a temporal relationship between eye movement, head movement and shoulder movement of a user.

FIG. 7 shows a natural temporal relationship between eye movement, head movement and shoulder movement of a user during active rotation of the user's body with respect to an onset of the respective movement after the user receives an auditory instruction to perform the respective movement(s). The eye movement was measured with an eye tracking device, the head movement was measured with a gyroscope integrated with a full-scalp EEG system and the shoulder movement was measured with a motion capture system. As can be seen in FIG. 7, the eye movement was detected, on average, 1.03 sec. [std: ±0.74 sec.] after onset of the stimulus, the head movement was detected, on average, 1.64 sec. [std: ±0.47 sec.] after onset of the stimulus, and the shoulder movement was detected, on average, 1.6 sec. [std: ±0.89 sec.] after onset of the stimulus. Hence, the eye movement occurred sooner than head movement and shoulder movement, respectively. Hence, the data provided in FIG. 7 may be used to determine a natural correlation between eye movement, head movement and shoulder movement. One or more deviations from said natural correlation may be determined as a user intent.

Figure 8:
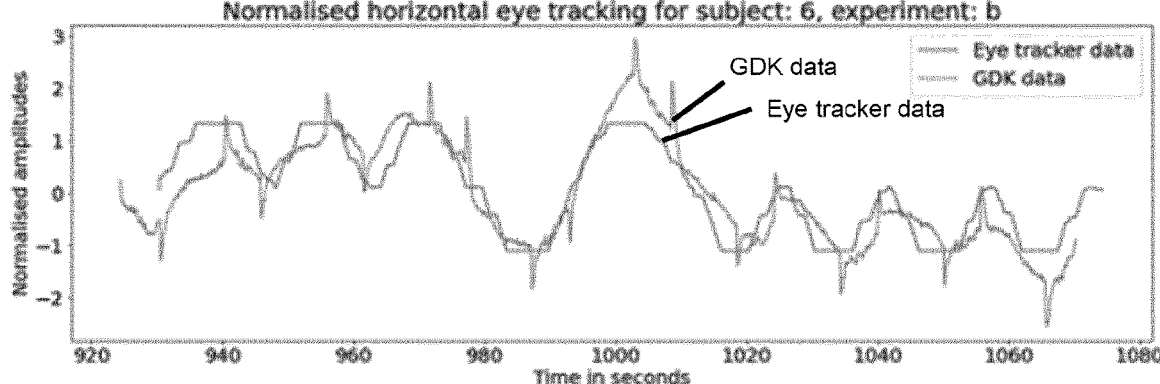
FIG. 8 shows an exemplary experiment which illustrates a comparison of an eye tracker known from the prior art and an in-ear detection device according to the present disclosure.

FIG. 8 shows an exemplary experiment in which eye movement was tracked via an eye tracker known from the prior art (eye tracker data) and via an in-ear detection device (GDK data) configured to sense an electrooculographic signal (EOG) in an ear of a user, e.g., which the eye movement sensing device 19 described herein may be configured as. The respective signals are indicated as normalised amplitudes and are shown in comparison with each other in FIG. 8. As can be seen from FIG. 8, the eye tracker may periodically lose track of the eye, as indicated by the plateaus, i.e., the straight horizontal lines, in the signal of the eye tracker, whereas the in-ear detection device may be able to track the eye, i.e., at least some polar differences, in the aforementioned regions of the signals. Hence, the eye movement sensing device 19 configured to sense an electrooculographic signal (EOG), in particular in-ear, may provide a more reliable and/or a more accurate detection of eye movement than eye trackers known from the prior art.

While various embodiments of the present disclosure have been described above, it should be understood that they have been presented by way of example only, and not by way of limitation. Likewise, the various diagrams may depict an example architectural or configuration, which are provided to enable persons of ordinary skill in the art to understand exemplary features and functions of the present disclosure. Such persons would understand, however, that the present disclosure is not restricted to the illustrated example architectures or configurations, but can be implemented using a variety of alternative architectures and configurations. Additionally, as would be understood by persons of ordinary skill in the art, one or more features of one embodiment can be combined with one or more features of another embodiment described herein. Thus, the breadth and scope of the present disclosure should not be limited by any one of the above-described exemplary embodiments.

It is also understood that any reference to an element herein using a designation such as "first," "second," and so forth does not generally limit the quantity or order of those elements. Rather, these designations can be used herein as a convenient means of distinguishing between two or more elements or instances of an element. Thus, a reference to first and second elements does not mean that only two elements can be employed, or that the first element must precede the second element in some manner.

Additionally, a person having ordinary skill in the art would understand that information and signals can be represented using any one of a variety of different technologies and techniques. For example, data, instructions, commands, information, signals, bits and symbols, for example, which may be referenced in the above description can be represented by voltages, currents, electromagnetic waves, magnetic fields or particles, optical fields or particles, or any combination thereof.

A skilled person would further appreciate that any one of the various illustrative logical blocks, units, processors, means, circuits, methods and functions described in connection with the aspects disclosed herein can be implemented by electronic hardware (e.g., a digital implementation, an analog implementation, or a combination of the two), firmware, various forms of program or design code incorporating instructions (which can be referred to herein, for convenience, as "software" or a "software unit"), or any combination of these techniques.

To clearly illustrate this interchangeability of hardware, firmware and software, various illustrative components, blocks, units, circuits, and steps have been described above generally in terms of their functionality. Whether such functionality is implemented as hardware, firmware or software, or a combination of these techniques, depends upon the particular application and design constraints imposed on the overall system. Skilled artisans can implement the described functionality in various ways for each particular application, but such implementation decisions do not cause a departure from the scope of the present disclosure. In accordance with various embodiments, a processor, device, component, circuit, structure, machine, unit, etc. can be configured to perform one or more of the functions described herein. The term "configured to" or "configured for" as used herein with respect to a specified operation or function refers to a processor, device, component, circuit, structure, machine, unit, etc. that is physically constructed, programmed and/or arranged to perform the specified operation or function.

Furthermore, a skilled person would understand that various illustrative logical blocks, units, devices, components and circuits described herein can be implemented within or performed by an integrated circuit (IC) that can include a general purpose processor, a digital signal processor (DSP), an application specific integrated circuit (ASIC), a field programmable gate array (FPGA) or other programmable logic device, or any combination thereof. The logical blocks, units, and circuits can further include antennas and/or transceivers to communicate with various components within the device. A general purpose processor can be a microprocessor, but in the alternative, the processor can be any conventional processor, controller, or state machine. A processor can also be implemented as a combination of computing devices, e.g., a combination of a DSP and a microprocessor, a plurality of microprocessors, one or more microprocessors in conjunction with a DSP core, or any other suitable configuration to perform the functions described herein. If implemented in software, the functions can be stored as one or more instructions or code on a computer-readable medium. Thus, the steps of a method or algorithm disclosed herein can be implemented as software stored on a computer-readable medium.

Computer-readable media includes both computer storage media and communication media including any medium that can be enabled to transfer a computer program or code from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer.

In this document, the term "unit" as used herein, refers to software, firmware, hardware, and any combination of these elements for performing the associated functions described herein. Additionally, for purpose of discussion, the various units are described as discrete units; however, as would be apparent to one of ordinary skill in the art, two or more units may be combined to form a single unit that performs the associated functions according embodiments of the present disclosure.

Additionally, memory or other storage, as well as communication components, may be employed in embodiments of the present disclosure. It will be appreciated that, for clarity purposes, the above description has described embodiments of the present disclosure with reference to different functional units and processors. However, it will be apparent that any suitable distribution of functionality between different functional units, processing logic elements or domains may be used without detracting from the present disclosure. For example, functionality illustrated to be performed by separate processing logic elements, or controllers, may be performed by the same processing logic element, or controller. Hence, references to specific functional units are only references to a suitable means for providing the described functionality, rather than indicative of a strict logical or physical structure or organization.

Various modifications to the implementations described in this disclosure will be readily apparent to those skilled in the art, and the general principles defined herein can be applied to other implementations without departing from the scope of the claims. Thus, the disclosure is not intended to be limited to the implementations shown herein, but is to be accorded the widest scope consistent with the novel features and principles disclosed herein, as recited in the claims below.

The invention claimed is:

1. An apparatus for determining at least one intent of at least one user, the apparatus comprising:

at least one eye movement sensing device configured to sense at least one eye movement signal from the user, the eye movement signal being indicative of at least one eye movement of the user; and at least one head movement sensing device configured to sense at least one head movement signal from the user, the head movement signal being indicative of at least one head movement of the user;

wherein the apparatus is configured to determine at least one degree of correlation between the eye movement signal and the head movement signal, wherein the apparatus is configured to determine at least one intent of the user based at least on the determined degree of correlation, wherein the eye movement sensing device is configured to sense at least one bioelectrical signal from the user, the bioelectrical signal being indicative of at least one eye movement of the user, wherein the apparatus is configured to distinguish between a plurality of different intents and to classify the intent of the user into a plurality of different classes based on one or more criteria that the determined degree of correlation must satisfy in order to be classified into the respective class, wherein the apparatus comprises or is coupled to an electronic media device, wherein the apparatus is configured to provide at least one control input to control at least one function of the electronic media device based on the determined intent of the user, and wherein the apparatus is configured to control, by the at least one control input, at least one of the following functions of the electronic media device: a volume, a light intensity, a 2D or 3D distribution of sound, an audio content, a spatial variance of one or more properties of an audio, one or more functions of a lighting device of the electronic media device, one or more functions of an audio device of the electronic media device, and activation/deactivation of the electronic media device.

2. The apparatus according to claim 1, wherein the bioelectrical signal is a biopotential signal.

3. The apparatus according to claim 1, further comprising at least one earpiece configured to be worn on the user's ear(s) and/or over the user's ear(s) and/or at least partially within a cavity of the user's ear(s), wherein the earpiece comprises at least the eye movement sensing device and/or the head movement sensing device.

4. The apparatus according to claim 3, wherein the earpiece comprises at least one eartip configured to be inserted at least partially into a cavity of the user's ear, wherein the eartip includes at least the eye movement sensing device, wherein the eartip is configured such that the eye movement sensing device is at least partially inserted into the cavity of the user's ear, when the eartip is inserted at least partially into the cavity of the user's ear.

5. The apparatus according to claim 1, wherein the apparatus is configured to classify the intent of the user by determining whether the determined degree of correlation satisfies at least one criterion.

6. The apparatus according to claim 5, wherein the apparatus is configured to determine whether the determined correlation is a natural correlation between the sensed eye movement and the sensed head movement of the user or an unnatural correlation between the sensed eye movement and the sensed head movement of the user according to at least one criterion to classify the intent of the user based thereon.

7. The apparatus according to claim 1, wherein the apparatus is configured to determine a natural correlation between the sensed eye movement and the sensed head movement of the user by determining a threshold representing a minimum degree of head movement of the user based on the sensed eye movement of the user and subsequently determining if the threshold is reached and/or surpassed by the sensed head movement.

8. The apparatus according to claim 1, wherein the apparatus is configured to determine a natural correlation between the sensed eye movement and the sensed head movement of the user by determining a direction of the sensed head movement of the user and a target direction of head movement of the user based on the sensed eye movement of the user and determining if the determined direction of the sensed head movement of the user and the target direction of head movement of the user substantially match and/or are within a target range.

9. The apparatus according to claim 1, wherein the apparatus is configured to determine a first intent, when the determined correlation satisfies at least one first criterion, and a second intent, when the determined correlation satisfies at least one second criterion, the first criterion differing from the second criterion and/or the first intent differing from the second intent.

10. A method for determining at least one intent of at least one user using the apparatus according to claim 1, the method comprising the following steps:

sensing at least one eye movement signal from the user using at least one eye movement sensing device the eye movement signal being indicative of at least one eye movement of the user, wherein the eye movement sensing device is configured to sense at least one bioelectrical signal from the user, the bioelectrical signal being indicative of at least one eye movement of the user;

sensing at least one head movement signal from the user using at least one head movement sensing device, the head movement signal being indicative of at least one head movement of the user;

determining at least one degree of correlation between the eye movement signal and the head movement signal;

determining at least one intent of the user based at least on the determined degree of correlation;

distinguishing between a plurality of different intents and classifying the intent of the user into a plurality of different classes based on one or more criteria that the determined degree of correlation must satisfy in order to be classified into the respective class; and generating at least one control input to control at least one function of at least one electronic media device based on the determined intent of the user, wherein the apparatus comprises or is coupled to the electronic media device, wherein the apparatus is configured to control, by the at least one control input, at least one of the following functions of the electronic media device: a volume, a light intensity, a 2D or 3D distribution of sound, an audio content, a spatial variance of one or more properties of an audio, one or more functions of a lighting device of the electronic media device, one or more functions of an audio device of the electronic media device, and activation/deactivation of the electronic media device.

11. The method according to claim 10, wherein the intent of the user is classified by determining whether the determined correlation is a natural correlation between the sensed eye movement and the sensed head movement of the user or an unnatural correlation between the sensed eye movement and the sensed head movement of the user.

12. The method according to claim 10, wherein a first intent is determined, when the determined correlation satisfies at least one first criterion, and a second intent is determined, when the determined correlation satisfies at least one second criterion, the first criterion differing from the second criterion and/or the first intent differing from the second intent.

13. The apparatus according to claim 1, wherein the bioelectrical signal is an electrooculographic (EOG) signal.

\* \* \* \* \*